US008809382B2

(12) United States Patent
Powell et al.

(10) Patent No.: US 8,809,382 B2
(45) Date of Patent: Aug. 19, 2014

(54) 5-OXO-ETE RECEPTOR ANTAGONIST COMPOUNDS

(75) Inventors: William S. Powell, Laval (CA); Joshua Rokach, Indian Harbour Beach, FL (US)

(73) Assignees: The Royal Institution for the Advancement of Learning/McGill University, Montreal, Quebec (CA); Florida Institute of Technology, Melbourne, FL (US)

( * ) Notice: Subject to any disclaimer, the term of this patent is extended or adjusted under 35 U.S.C. 154(b) by 30 days.

(21) Appl. No.: 13/318,697

(22) PCT Filed: May 4, 2010

(86) PCT No.: PCT/CA2010/000699
§ 371 (c)(1),
(2), (4) Date: Jan. 30, 2012

(87) PCT Pub. No.: WO2010/127452
PCT Pub. Date: Nov. 11, 2010

(65) Prior Publication Data
US 2012/0122942 A1  May 17, 2012

Related U.S. Application Data

(60) Provisional application No. 61/175,175, filed on May 4, 2009, provisional application No. 61/289,062, filed on Dec. 22, 2009.

(51) Int. Cl.
*A61K 31/405* (2006.01)
*C07D 209/12* (2006.01)
*C07D 403/06* (2006.01)

(52) U.S. Cl.
CPC ............ *C07D 209/12* (2013.01); *C07D 403/06* (2013.01)
USPC ............ 514/381; 514/419; 548/253; 548/494

(58) Field of Classification Search
USPC ....................................................... 548/494
See application file for complete search history.

(56) References Cited

U.S. PATENT DOCUMENTS

| 3,238,215 | A | 3/1966 | Archibald et al. |
| 6,200,978 | B1 | 3/2001 | Maw et al. |
| 2005/0245593 | A1 | 11/2005 | Sundermann et al. |
| 2008/0188532 | A1 | 8/2008 | Takeuchi et al. |

FOREIGN PATENT DOCUMENTS

| SU | 513032 | 12/1974 |
| WO | WO 96/32379 A1 | 10/1996 |
| WO | WO 2006/046683 | 5/2006 |
| WO | WO 2009/005998 | 1/2009 |

OTHER PUBLICATIONS

Bell. Document No. 87:152012, retrieved from CAPLUS, May 12, 1984.*
Dubovitskii. Document No. 125:167674, retrieved from CAPLUS, Aug. 1, 1996.*
Gromov, et al. Document No. 125:195337, retrieved from CAPLUS, Jul. 10, 1996.*
Khdour, et al. Document No. 145:230207, retrieved from CAPLUS, Jul. 18, 2006.*
Kost, et al. Document No. 81:120366, retrieved from CAPLUS, May 12, 1984.*
Li, et al. Document No. 148:355589, retrieved from CAPLUS, Jan. 31, 2008.*
Liu, et al. Document No. 148:379473, retrieved from CAPLUS, Feb. 27, 2008.*
Okada, et al. Document No. 116:128657, retrieved from CAPLUS, Apr. 3, 1992.*
Teuber, et al. Document No. 60:52627, retrieved from CAPLUS, Apr. 22, 2001.*
What Is COPD? [online], retrieved from the internet on Apr. 25, 2013. URL; http://www.nhlbi.nih.gov/health/health-topics/topics/copd/.*
N. Prasipan et al., "N-1 and C-2 Substituted Tryptophans As Potential Inhibitors of Sickle Cell Hemoglobin Gelation", Journal of Heterocyclic Chemistry, vol. 29, No. 2, Mar. 1, 1992, pp. 335-341.
Extended Search Report issued by European Patent Office on Dec. 11, 2012 in European Application No. 10771945.2 (13 pgs).
International Search Report (PCT/ISA/210) issued on Jul. 28, 2010, by Canadian Patent Office as the International Searching Authority for International Application No. PCT/CA2010/000699.
Written Opinion (PCT/ISA/237) issued on Jul. 28, 2010, by Canadian Patent Office as the International Searching Authority for International Application No. PCT/CA2010/000699.
Scott et al., "Indole as a Dienophile in Inverse Electron Demand Diels-Alder Reactions. 3. Intramolecular Reactions with 1,2,4-Triazines to Access the Canthine Skeleton", Journal of Organic Chemistry, 1992, pp. 5285-5287.
Krauss et al., "Intramolecular Diels-Alder Reactions of Indoles", Tetrahedron Letters, 1998, pp. 5605-5608, vol. 29, No. 44.

* cited by examiner

*Primary Examiner* — Shawquia Young
(74) *Attorney, Agent, or Firm* — Buchanan Ingersoll & Rooney P.C.

(57) ABSTRACT

The present invention relates to novel pharmaceutically-useful compounds which are antagonists of the 5-oxo-ETE receptors, such as the OXE receptor. These compounds have use as therapeutic and/or prophylactic agents for diseases characterized by tissue eosinophilia, such as inflammatory conditions including respiratory diseases. The invention also relates to pharmaceutical compositions, to the use of such compounds and compositions as medicaments, and to therapeutic methods.

15 Claims, 5 Drawing Sheets

5-OXO-ETE RECEPTOR ANTAGONIST COMPOUNDS

FIELD OF THE INVENTION

This invention relates to novel pharmaceutically-useful compounds which are antagonists of a G-protein coupled eicosanoid receptor, to methods for their preparation, and to pharmaceutical compositions and therapeutic methods for treating eicosanoid-mediated disorders such as inflammatory and allergic conditions.

BACKGROUND OF THE INVENTION

Arachidonic acid is a key biological intermediate that is converted to a large number of eicosanoids with potent biological activities. Metabolism of arachidonic acid by the 5-lipoxygenase (5-LO) pathway leads to the formation of leukotrienes such as $LTB_4$, $LTC_4$ and $LTD_4$, and 5S-hydroxy-6E,8Z,11Z,14Z-eicosatetraenoic acid (5-HETE). 5-HETE is oxidized to 5-oxo-6,8,11,14-eicosatetraenoic acid (5-oxo-ETE) by the action of 5-hydroxyeicosanoid dehydrogenase, a microsomal enzyme found in leukocytes and platelets, as well as endothelial and epithelial cells.

5-Oxo-ETE is a potent chemoattractant for eosinophils and neutrophils, and elicits a variety of rapid responses in these cells. Examples of the responses in these cells in addition to cell migration and tissue infiltration include actin polymerization, calcium mobilization, integrin expression, shedding of L-selectin, degranulation, and superoxide production. The primary target of 5-oxo-ETE is most likely the eosinophil, and among lipid mediators it is the strongest chemoattractant for these cells. It has been shown to induce transendothelial migration of eosinophils and to induce the infiltration of both eosinophils and neutrophils into the skin. 5-Oxo-ETE also promotes the survival of eosinophils and possibly other types of inflammatory cells through, for example, the induction of GM-CSF release from monocytes. 5-Oxo-ETE is also a chemoattractant for monocytes and has been shown to stimulate the proliferation of prostate tumor cells.

The biological effects of 5-oxo-ETE are mediated by a G, protein-coupled receptor termed the OXE receptor. This receptor is expressed on eosinophils, neutrophils, and monocytes, as well as on prostate tumor cells.

Eicosanoids produced by the 5-LO pathway are known to be important mediators for inflammatory and allergic diseases such as asthma, allergic rhinitis, chronic obstructive pulmonary disorder, atopic dermatitis and acne, and have been shown to play a role in certain cancers such as prostate cancer. The biological effects of 5-oxo-ETE suggest that agents which block its action may function as therapeutic or prophylactic agents for such diseases. It would be desirable therefore to be provided with antagonists of the 5-oxo-ETE receptors, such as the OXE receptor.

SUMMARY OF THE INVENTION

The present invention relates to novel compounds having activity as antagonists of the 5-oxo-ETE receptors (for example the OXE receptor), to methods for their preparation, to pharmaceutical compositions containing the compounds, and to methods for using these compounds in mammals, especially humans, to treat or prevent inflammatory conditions such as respiratory diseases like asthma. Because of their activity as 5-oxo-ETE receptor antagonists, the compounds of the present invention are useful as anti-asthmatic, anti-allergic, and anti-inflammatory agents, as well as agents for the treatment or prevention of cancer, e.g. lung, pancreatic and/or prostate cancer.

In accordance with the present invention, there are provided herein heterocyclic and aromatic compounds having the general formula (I), their preparation, and pharmaceutical compositions thereof. The invention also pertains to the use of such compounds and compositions as antagonists of the 5-oxo-ETE receptors.

In at least one aspect, the invention therefore relates to heterocyclic compounds having the general formula (I):

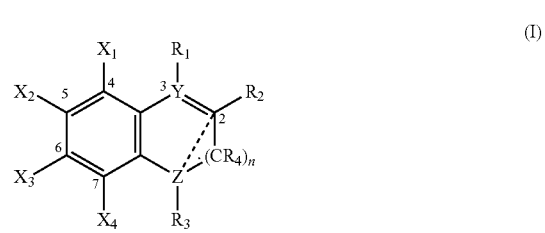

wherein:

$X_1$, $X_2$, $X_3$ and $X_4$ are independently selected from the group consisting of H, halogen, alkyl, aralkyl and $OR_5$ wherein $R_5$ is selected from the group consisting of H, acyl, alkyl, aralkyl, alkenyl, alkoxy, aryl, haloalkyl, cycloalkyl, haloalkoxy, heterocycloalkyl, cycloalkenyl and heterocycloalkenyl, any of which may be optionally substituted;

n is 0 or 1 provided that when n=0, Z and $C_2$ are operatively linked by a bond;

Z is N, O, S, or C;

Y is C or N, provided that when Z is O or S, then Y is C; and $R_1$, $R_2$, $R_3$ and $R_4$ are independently selected from H and alkyl, said alkyl optionally interrupted by one or more heteroatoms or carbonyl groups and optionally substituted with OH, SH, $COOR_6$, $NR_6R_7$, a C6-16 aryl, a C6-16 heterocycle, a C3-7 cycloalkyl, a heterocyclic ring or a hydrophobic group, wherein $R_6$ and $R_7$ are a C6-16 aryl, C6-16 heterocycle, C3-7 cycloalkyl, a heterocyclic ring or a hydrophobic group;

or a pharmaceutically acceptable salt thereof.

In another aspect, there are provided herein compounds having the general formula (I) wherein Z and Y are both N.

In another aspect, the invention relates to compounds having the Formula II:

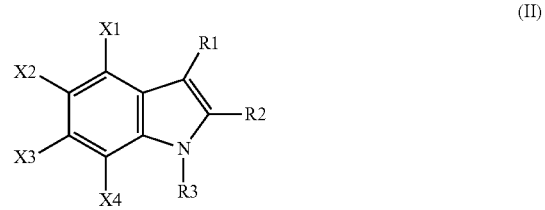

wherein X1, X2, X3, X4, R1, R2 and R3 are as defined above; or a pharmaceutically acceptable salt thereof.

In another aspect, the invention relates to compounds having the Formula III:

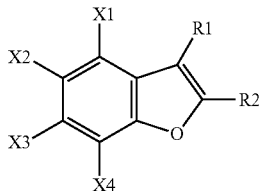

(III)

wherein X1, X2, X3, X4, R1, and R2 are as defined above; or a pharmaceutically acceptable salt thereof.

In another aspect, the invention relates to compounds having the Formula IV:

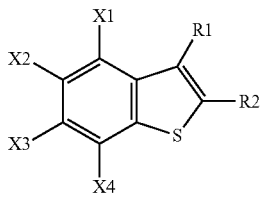

(IV)

wherein X1, X2, X3, X4, R1 and R2 are as defined above; or a pharmaceutically acceptable salt thereof.

In another aspect, the invention relates to compounds having the Formula V:

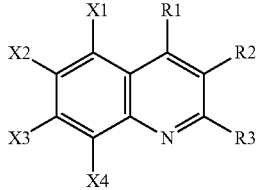

(V)

wherein X1, X2, X3, X4, R1, R2 and R3 are as defined above; or a pharmaceutically acceptable salt thereof.

In another aspect, the invention relates to compounds having the Formula VI:

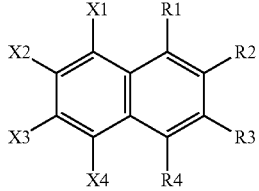

(VI)

wherein X1, X2, X3, X4, R1, R2, R3 and R4 are as defined above; or a pharmaceutically acceptable salt thereof.

In another aspect, the invention relates to compounds having the Formula VII:

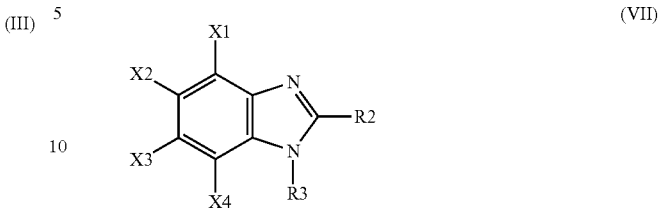

(VII)

wherein X1, X2, X3, X4, R2, and R3 are as defined above; or a pharmaceutically acceptable salt thereof.

In another aspect, the invention relates to compounds having the Formula VIII:

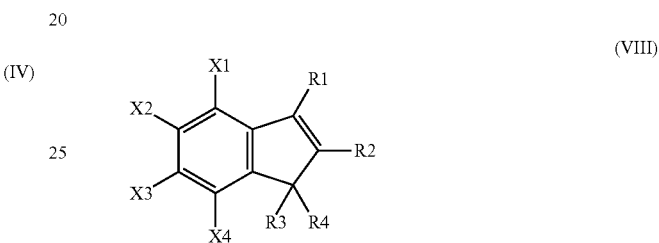

(VIII)

wherein X1, X2, X3, X4, R1, R2, R3 and R4 are as defined above; or a pharmaceutically acceptable salt thereof.

In another aspect, the invention relates to compounds having the Formula IX:

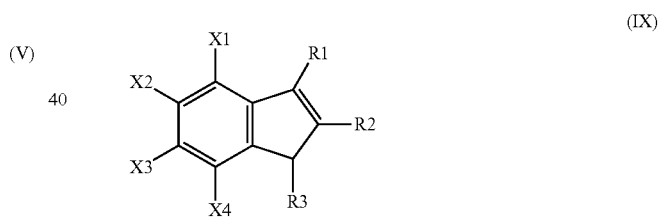

(IX)

wherein X1, X2, X3, X4, R1, R2, and R3 are as defined above; or a pharmaceutically acceptable salt thereof.

In yet another aspect, the invention relates to compounds as described above wherein R1 to R4 are independently hydrogen or a carboxyl side chain selected from the group consisting of

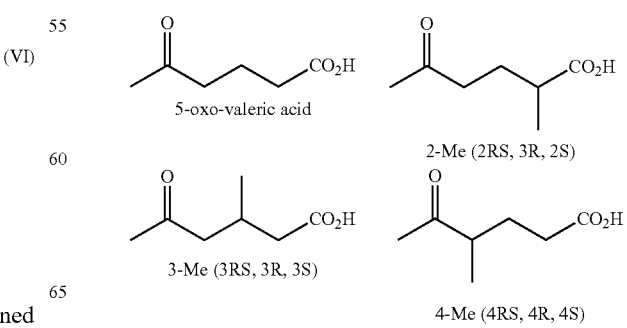

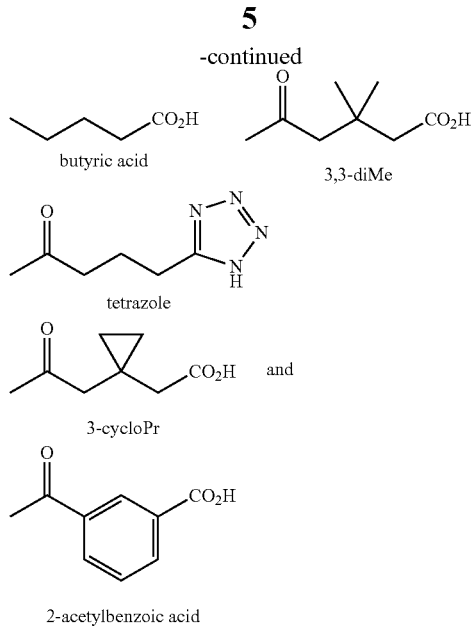

In a further aspect, the invention relates to compounds as described above wherein R1 to R4 are independently hydrogen or an alkyl group selected from the group consisting of butyl, pentyl, hexyl, 1-hexenyl, heptyl, octyl, undecyl, 1-undecenyl, 6,6-dimethylhexyl, 5-methylhexyl, 4-methylhexyl, 4-phenylbutyl, 4-cyclohexylbutyl, 4-cyclopentylbutyl, 6,6,6-trifluorohexyl, t-butylhexyl, phenylbutyl, cyclohexylbutyl and cyclopentylbutyl.

In a yet further aspect, the invention relates to compounds as described above wherein the aromatic group in the compound is substituted with halogen.

In another aspect, the invention relates to compounds shown in Table 1 herein, or pharmaceutically acceptable salts thereof.

Pharmaceutical compositions comprising a therapeutically effective amount of the compounds disclosed herein and a pharmaceutically acceptable carrier are also provided.

In another aspect, the invention relates to methods of treating or preventing inflammation or a disease associated with inflammation in a subject by administering to the subject a therapeutically effective amount of the compounds or compositions described herein. In an aspect the disease associated with inflammation may be asthma, allergic rhinitis, COPD or idiopathic pulmonary fibrosis. There are also provided herein methods of treating or preventing asthma in a subject by administering to the subject a therapeutically effective amount of the compounds or compositions described herein. Methods of treating or preventing a respiratory condition in a subject by administering to the subject a therapeutically effective amount of the compounds or compositions described herein are also provided. Such respiratory conditions may or may not be associated with inflammation. In yet another aspect, methods of inhibiting the action of eicosanoids in a subject by administering to the subject an effective amount of the compounds or compositions described herein are provided. In one aspect, the eicosanoid is 5-oxo-ETE. A subject may be suffering from or susceptible to the disease or condition being treated or prevented.

Also provided herein are therapeutics methods wherein a subject is treated by concomitant administration of a compound or composition as disclosed herein and a second agent. A second agent may be administered at the same time as the compound or composition of the invention or the two may be administered sequentially. In one aspect, the second agent is an analgesic, anti-inflammatory agent or anti-allergy agent, for example an NSAID, a bronchodilator or a leukotriene modifier.

BRIEF DESCRIPTION OF THE DRAWINGS

Having thus generally described the nature of the invention, reference will now be made to the accompanying drawings, showing by way of illustration, an embodiment or embodiments thereof, and in which.

DETAILED DESCRIPTION

Figure 1:
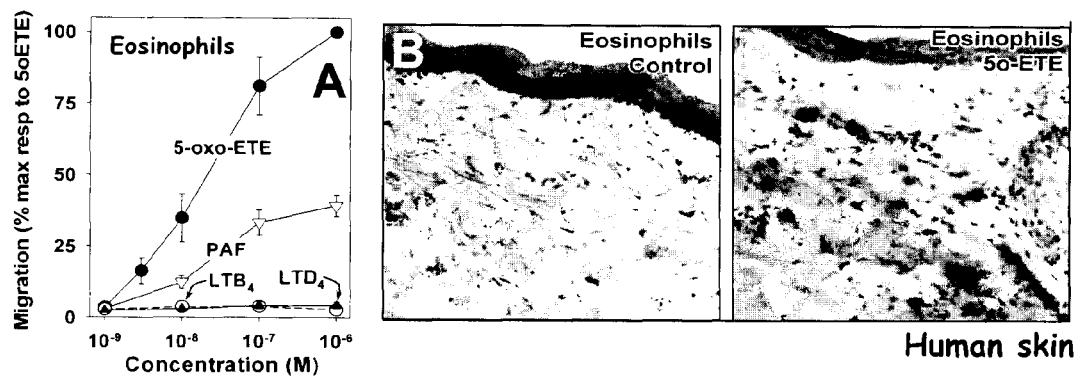
FIG. 1 shows the chemoattractant effects of 5-oxo-ETE on human eosinophils, wherein (A) shows in vitro effects of 5-oxo-ETE (5oETE) and other lipid mediators such as platelet activating factor (PAF) and leukotrienes $LTB_4$ and $LTD_4$ on eosinophil migration in Boyden chambers; and (B) control and (C) show effects of intradermal injection of 5-oxo-ETE on eosinophil infiltration into human skin after 24 h.
Figure 2:
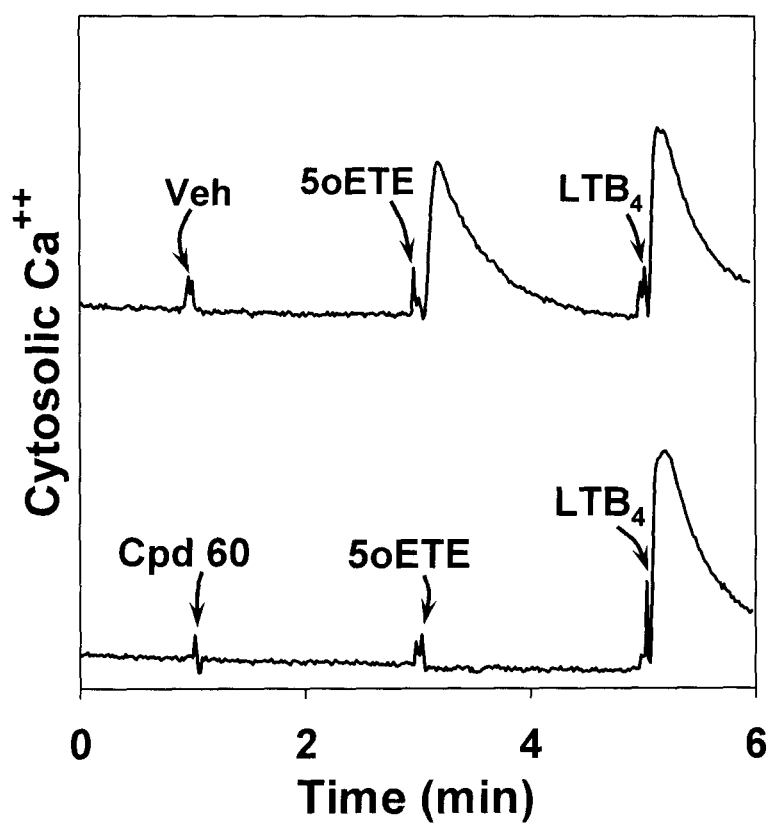
FIG. 2 shows the effects of compound #60 on 5-oxo-ETE-induced calcium mobilization in human neutrophils, wherein calcium transients in responses to 5-oxo-ETE (5oETE) and $LTB_4$ (10 nM of each) were not affected by vehicle (top), however compound #60 (1 μM) completely blocked calcium mobilization in response to 5-oxo-ETE but not to $LTB_4$.
Figure 3:
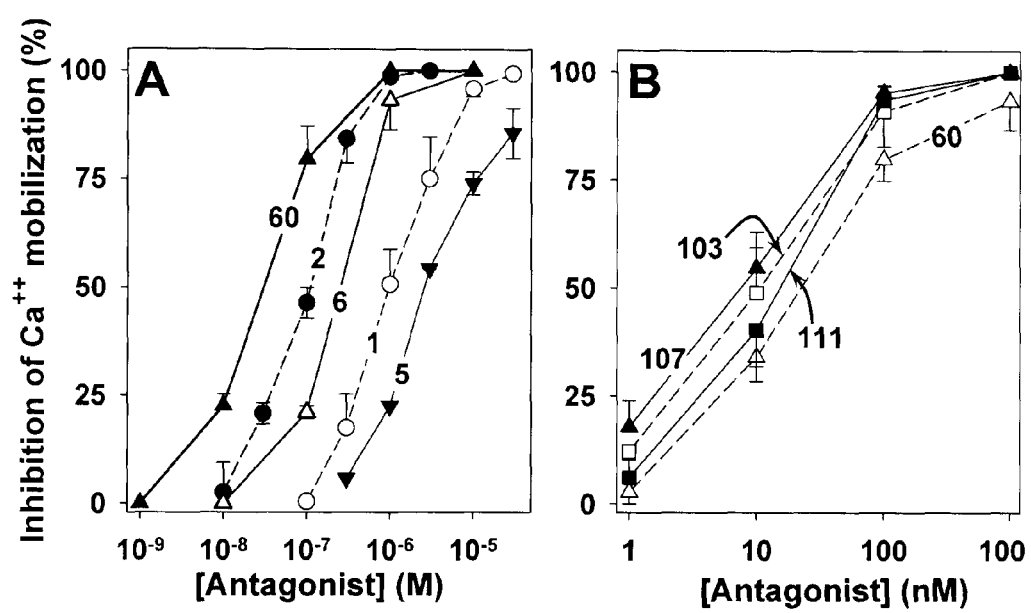
FIG. 3 shows the effects of OXE-R antagonists (compound #s are indicated) on $Ca^{++}$ mobilization in human neutrophils in response to 5-oxo-ETE (10 nM); an early series of compounds (#1, 2, 5, 6) along with the more potent compound #60 are shown in panel A, and the compounds (#60, 103, 107, and 111) are shown in panel B.
Figure 4:
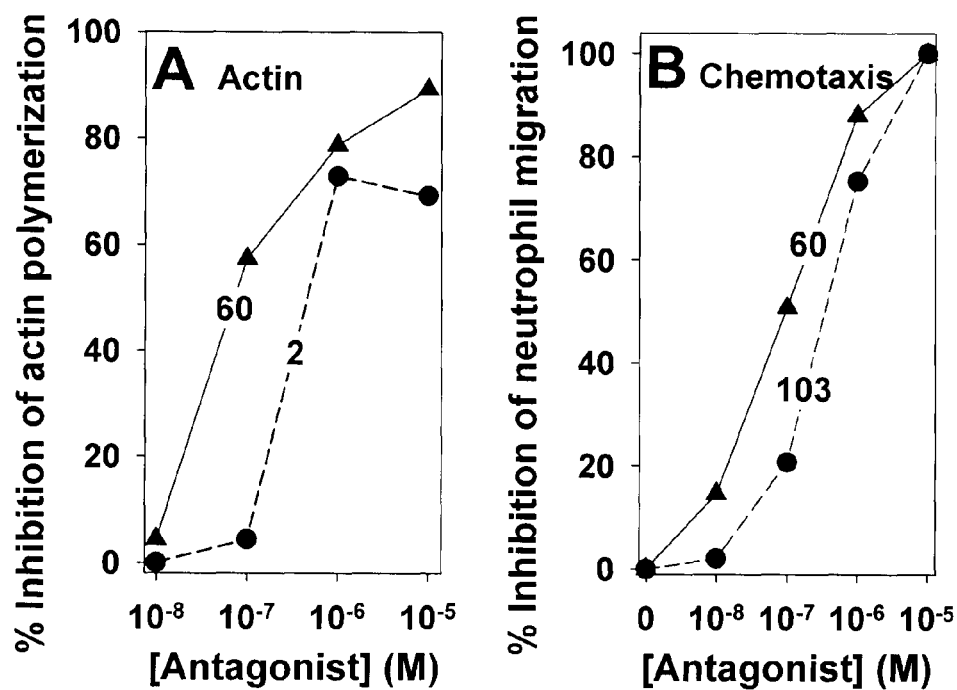
FIG. 4 shows the effects of 5-oxo-ETE antagonists on 5-oxo-ETE-induced actin polymerization and chemotaxis, wherein in (A) granulocytes were incubated with different concentrations of compound #60 (▲) and compound #2 (•) for 5 min and then incubated with 5-oxo-ETE for a further 20 s; actin polymerization was measured in eosinophils by flow cytometry; and in (B) the effects of compound #60 (▲) and compound #103 (•) on neutrophil migration induced by 5-oxo-ETE (100 nM) was measured in microchemotaxis chambers.
Figure 5:
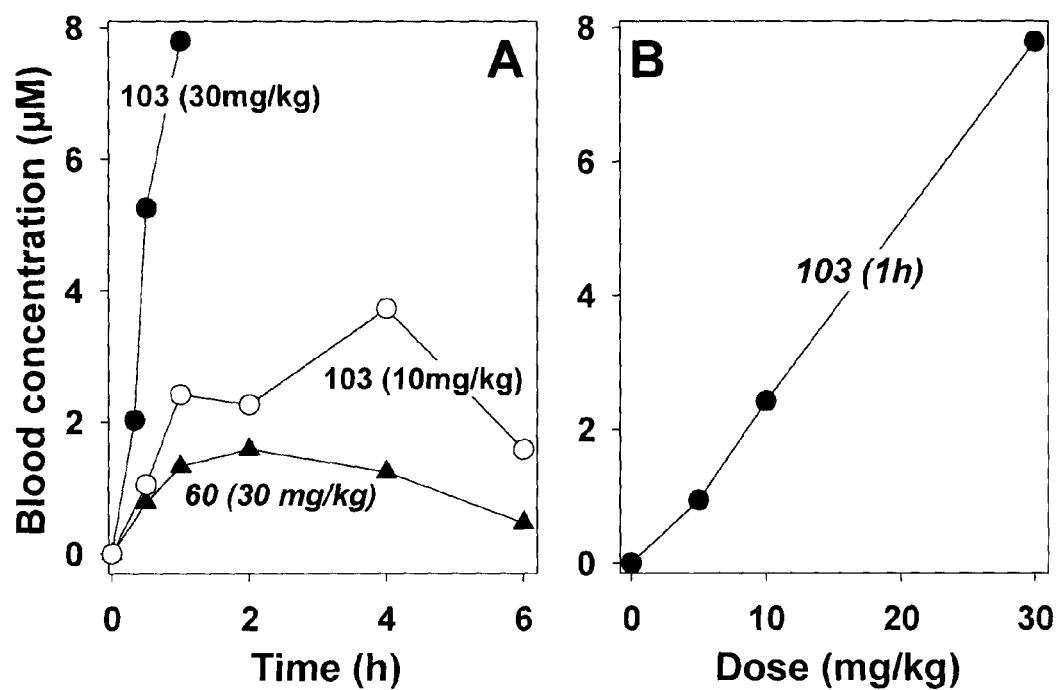
FIG. 5 shows the concentrations of compounds #60 and 103 in blood following oral administration by gavage. Panel A: Cpd #60 was measured for up to 6 h following administration of a dose of 30 mg/kg (▲), whereas compound #103 was measured for 1 h after an identical dose (•). The blood levels of compound #103 were also measured for up to 6 h after a dose of 10 mg/kg (○). Panel B: The levels of compound #103 were measured in blood 1 h after oral administration of doses of 5, 10, and 30 mg/kg.

We report herein a series of novel synthetic compounds that act as antagonists of the 5-oxo-ETE receptors, such as the OXE receptor, and block biological responses to eicosanoids such as 5-oxo-ETE. These compounds represent the first 5-oxo-ETE receptor antagonists identified. Because of their activity as 5-oxo-ETE receptor antagonists, these compounds have use as therapeutic and/or prophylactic agents for any disease involving eosinophil or neutrophil infiltration into tissue or characterized by tissue eosinophilia. For example, the compounds and compositions of the present invention are useful as anti-asthmatic, anti-allergic, and anti-inflammatory agents.

As used herein, a "receptor antagonist" is a compound having the ability to inhibit the intracellular signal transduction caused by a stimulation of the receptor by a ligand.

Receptor antagonists may act by a variety of mechanisms, such as blocking binding of a ligand to the receptor, blocking activation of the receptor by a ligand, and so on.

Compounds of the Invention

The present invention relates to heterocyclic and aromatic compounds that inhibit the 5-Oxo-ETE receptors. These molecules are characterized by the general formula (I):

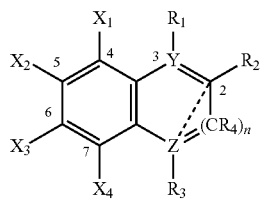

(I)

wherein:
$X_1$, $X_2$, $X_3$ and $X_4$ are independently selected from the group consisting of H, halogen, alkyl, aralkyl group and $OR_5$ wherein $R_5$ is selected from the group consisting of H, acyl, alkyl, aralkyl, alkenyl, alkoxy, aryl, haloalkyl, cycloalkyl, haloalkoxy, heterocycloalkyl, cycloalkenyl and heterocycloalkenyl, any of which may be optionally substituted;
n is 0 or 1 provided that when n=0, Z and $C_2$ are operatively linked by a bond;
Z is N, O, S, or C;
Y is C or N, provided that when Z is O or S, then Y is C; and
$R_1$, $R_2$, $R_3$ and $R_4$ are independently selected from H and alkyl, said alkyl optionally interrupted by one or more heteroatoms or carbonyl groups and optionally substituted with OH, SH, $COOR_6$, $NR_6R_7$, a $C_{6-16}$ aryl or heterocycle or $C_{3-7}$ cycloalkyl or heterocyclic ring or a hydrophobic group, wherein $R_6$ and $R_7$ are a $C_{6-16}$ aryl or heterocycle or $C_{3-7}$ cycloalkyl or a heterocyclic ring or a hydrophobic group;
or a pharmaceutically acceptable salt thereof.

In one embodiment, Z and Y are both N.

The term "hydrophobic group" (HG) as used hereinafter, refers to any group which lacks affinity for, or displaces water. Hydrophobic groups include but are not limited to $C_{1-20}$ alkyl, $C_2$-alkenyl (e.g. vinyl, allyl) or $C_{2-20}$ alkynyl (e.g. propargyl), optionally interrupted by a carbonyl group, (e.g. forming an acyl group), $C_{6-16}$ aryl, $C_{3-7}$ cycloalkyl, $C_{6-20}$ aralkyl, $C_{6-20}$ cycloalkyl substituted with $C_{1-20}$ alkyl, wherein the aliphatic portion is optionally interrupted by a carbonyl group (e.g. forming an acyl group) and the ring portion is optionally substituted with $C_{1-6}$ alkyl such as methyl, ethyl or t-butyl; or a hydrophobic amino acid side chain. Preferred hydrophobic groups include cyclohexyl, benzyl, benzoyl, phenylmethyl, phenethyl and para-t-butyl-phenylmethyl.

The term "halogen" means a halogen atom such as fluorine, chlorine, bromine, or iodine.

The term "alkyl" represents a straight or branched, saturated or unsaturated chain having a specified total number of carbon atoms. Examples of alkyl groups include, but are not limited to, $C_{1-10}$ alkyl groups. Examples of $C_{1-10}$ alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl and decyl.

The term "acyl group" is intended to mean a group having the formula RC=O, wherein R is an alkyl, alkenyl, cycloalkyl, heterocycloalkyl, cycloalkenyl, heterocycloalkenyl, or an aryl group.

The term "alkenyl" refers to a straight or branched chain alkyl moiety having two or more carbon atoms (e.g., two to six carbon atoms, $C_{2-6}$ alkenyl) and having in addition one double bond, of either E or Z stereochemistry where applicable. This term would include, for example, vinyl, 1-propenyl, 1- and 2-butenyl, 2-methyl-2-propenyl, etc.

The term "alkoxy" refers to straight-chain or branched alkyl groups having 1 to 10 carbon atoms as mentioned above, which are attached to the skeleton via an oxygen atom (—O—), for example $C_1$-$C_{10}$ alkoxy such as methyloxy, ethyloxy, propyloxy, 1-methylethyloxy, butyloxy, 1-methylpropyloxy, 2-methylpropyloxy, 1,1-dimethylethyloxy.

The term "aromatic" or "aryl" represents an unsaturated carbocyclic ring(s) of 5 to 16 carbon atoms which is optionally mono- or di-substituted with OH, SH, amino (i.e. $NR_6R_7$) halogen or $C_{1-8}$ alkyl. Aromatic rings include benzene, napthalene, phenanthrene and anthracene. Preferred aromatic rings are benzene and naphthalene.

The term "haloalkyl" refers to $C_1$-$C_{10}$ straight-chain or branched alkyl groups having 1 to 10 carbon atoms, it being possible for some or all of the hydrogen atoms in these groups to be replaced by halogen atoms as mentioned above, for example $C_1$-$C_{10}$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

The term "cycloalkyl" represents a carbocyclic ring of 3 to 7 carbon atoms which is optionally mono- or di-substituted with OH, SH, amino (i. e. $NR_6R_7$) halogen or $C_{1-8}$ alkyl. Cycloalkyl groups are generally saturated but may be partially unsaturated and include cyclo-propyl, butyl, pentyl, hexyl and heptyl. A preferred cycloalkyl group is cyclohexyl.

The term "aralkyl" represents a substituent comprising an aryl moiety attached via an alkyl chain (e.g. benzyl, phenethyl) wherein the sum total of carbon atoms for the aryl moiety and the alkyl chain is as specified. The aryl or chain portion of the group is optionally mono- or di-substituted with OH, SH, amino (i.e. $NR_6R_7$), halogen or $C_{1-8}$ alkyl.

The term "heteroatom" as used herein represents oxygen, nitrogen or sulfur (O, N or S) as well as sulfoxyl or sulfonyl (SO or $SO_2$) unless otherwise indicated. It is understood that alkyl chains interrupted by one or more heteroatoms means that a carbon atom of the chain is replaced with a heteroatom having the appropriate valency. Preferably, an alkyl chain is interrupted by 0 to 4 heteroatoms and the two adjacent carbon atoms are not both replaced.

The term "halo-alkoxy" refers to straight-chain alkyl groups having 2 to 10 carbon atoms, it being possible for some or all of the hydrogen atoms in these groups to be replaced by halogen atoms as mentioned above, these groups being attached to the skeleton via an oxygen atom, for example 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, and 2,2,2-trichloroethyloxy.

The term "heterocycle" or "heterocycloalkyl" represents a saturated or unsaturated mono- or polycyclic (i.e. bicyclic) ring incorporating 1 or more (i.e. 1-4) heteroatoms selected from N, O and S. It is understood that a heterocycle is optionally mono- or disubstituted with OH, SH, amino (i.e. $NR_6R_7$), halogen, CF₃, oxo or C₁₋₈, alkyl. Examples of suitable monocyclic heterocycles include but are not limited to pyridine, piperidine, pyrazine, piperazine, pyrimidine, imidazole, thiazole, oxazole, furan, pyran and thiophene. Examples of suitable bicyclic heterocycles include but are not limited to indole, benzimidazole, quinoline, isoquinoline and purine.

The term "cycloalkenyl" refers to an alicyclic moiety having three or more carbon atoms (e.g., from three to six carbon atoms) and having in addition one double bond. This term includes, for example, cyclopentenyl or cyclohexenyl.

The term "heterocycloalkenyl" refers to an alicyclic moiety having from three to six carbon atoms and one or more heteroatoms from the group N, O, S (or oxides thereof) and having in addition one double bond. This term includes, for example, dihydropyranyl.

The term "optionally substituted" means optionally substituted with one or more of the aforementioned groups (e.g., alkyl, aryl, heteroaryl, acyl, alkenyl, cycloalkyl, heterocycloalkyl, cycloalkenyl, heterocycloalkenyl, halogen or hydrophobic group), at any available position or positions.

The term "analog" is intended to mean a compound that is similar or comparable, but not identical, to a reference compound, i.e. a compound similar in function, structure, properties and/or appearance to the reference compound. As used herein, an analog is a chemical compound that may be structurally related to another but differs in composition (for example as in the replacement of one atom by an atom of a different element or in the presence of a particular functional group). An analog may be derived from a natural source or be prepared using chemical synthesis.

Other embodiments of the present invention are illustrated by compounds having the Formula II, III, IV, V, VI, VII, VIII or IX wherein R1, R2, R3, R4 and X1, X2, X3 and X4 are as defined as described above.

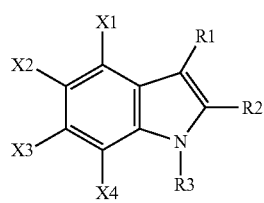

(II)

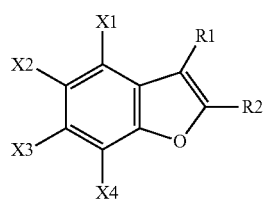

(III)

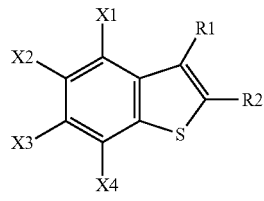

(IV)

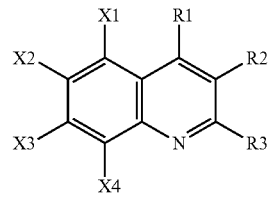

(V)

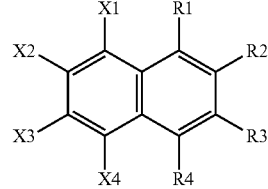

(VI)

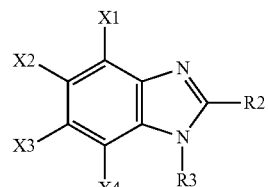

(VII)

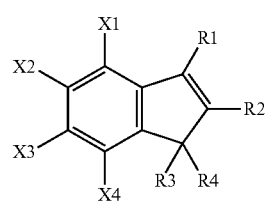

(VIII)

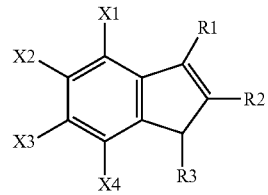

(IX)

It will be appreciated by those skilled in the art that compounds of formulae (I) to (IX), depending on the substituents, may contain one or more chiral centers and thus exist in the form of many different isomers, optical isomers (i.e. enantiomers) and mixtures thereof including racemic mixtures. All such isomers, enantiomers and mixtures thereof including racemic mixtures are included within the scope of the invention.

In one embodiment of the invention, the compounds of formulae (I) to (IX) are as follows: n=0; X1, X2, X3 and X 4 are independently H, Cl or CF₃; R1=H and R2 is a hydrophobic group as defined herein; R3 is a second hydrophobic group including but not limited to C₁₋₂₀ alkyl, C₂₋₂₀ alkynyl or C₂₋₂₀ alkynyl optionally interrupted by a carbonyl group (e.g. forming an acyl group with N; optionally interrupted by one or more chiral carbon atoms).

In another embodiment of the invention, the compounds of formulae (I) to (IX) are as follows: n=0; R3 is H, methyl or ethyl; R1 is a hydrophobic group as defined herein and R2 is a second hydrophobic group including but not limited to C₁₋₂₀ alkyl, C₂₋₂₀ alkynyl or C₂₋₂₀ alkynyl optionally interrupted by a carbonyl group (e.g. forming an acyl group with N; optionally interrupted by one or more chiral carbon atoms).

In the compounds of the invention, various substituents and modifications are contemplated as described above. For example, R1, R2, R3 and/or R4 may be a carboxyl side chain selected from the following:

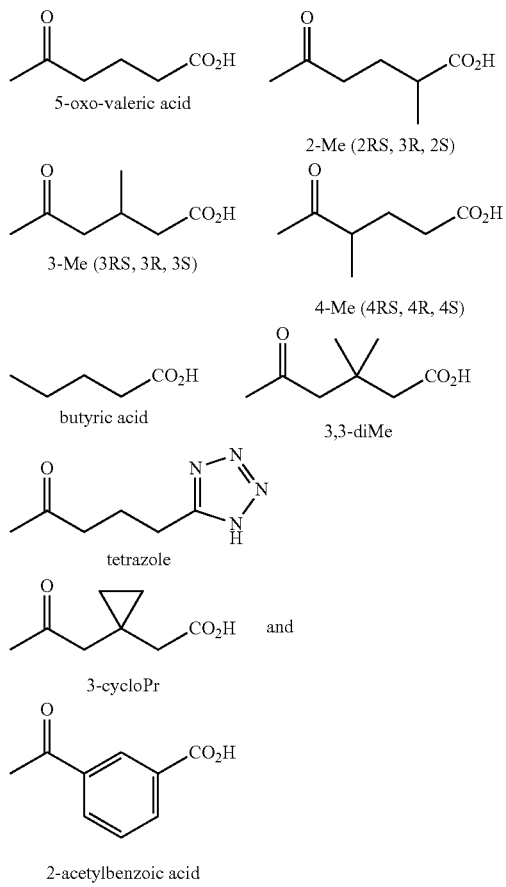

As another example, R1, R2, R3 and/or R4 may be an alkyl group selected from the following:

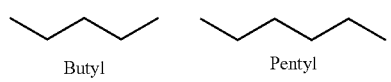

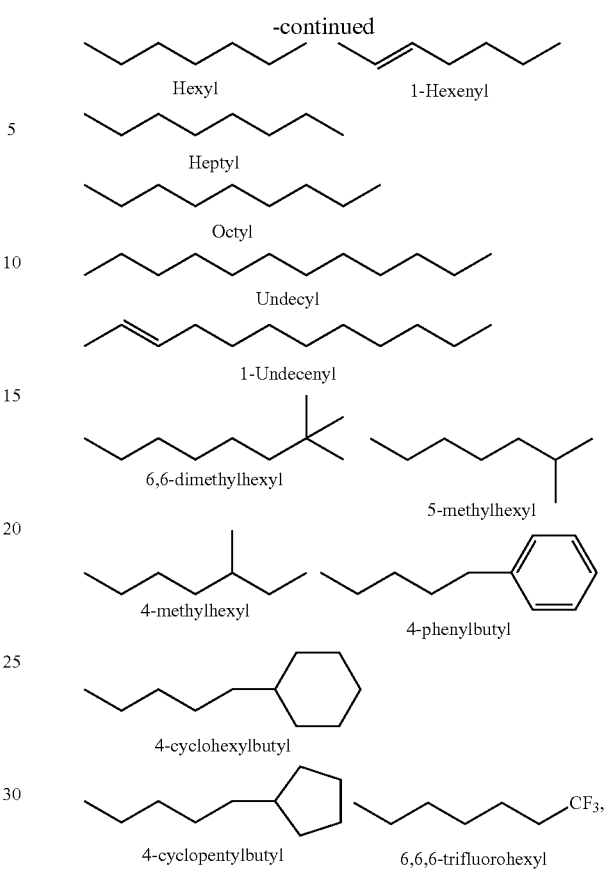

t-butylhexyl, phenylbutyl, cyclohexylbutyl, and cyclopentylbutyl.

In the compounds of the invention, the aromatic group may be optionally substituted with a halogen. As used herein, the term "halogen" includes F, Cl, Br or I.

It is intended that the definitions of any substituent (e.g. $R_1$, $R_2$, $R_3$, $R_4$, $X_1$, $X_2$, $X_3$, $X_4$) in a particular compound are independent of the definitions of the other substituents.

Substituents may be referred to with or without a subscript, for example "R1" or "$R_1$"; these terms are interchangeable.

Other representative compounds of the invention are shown in Table 1 below:

TABLE 1

Representative compounds of the invention

| Compound No. | Structure |
| --- | --- |
| 1 | 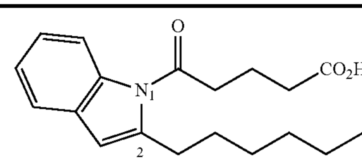 |
| 2 | 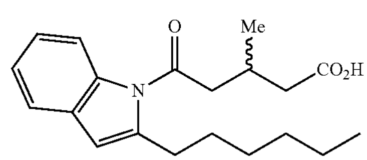 [SMILES: CCCCCCc1cc2ccccc2n1C(=O)CC(C)CC(=O)O] |

TABLE 1-continued

Representative compounds of the invention

| Compound No. | Structure |
| --- | --- |
| 3 | 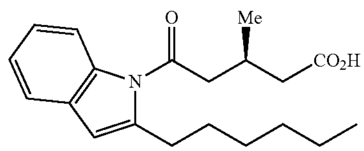 [SMILES: CCCCCCc1cc2ccccc2n1C(=O)C[C@@H](C)CC(=O)O] |
| 4 | 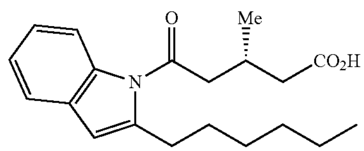 [SMILES: CCCCCCc1cc2ccccc2n1C(=O)C[C@H](C)CC(=O)O] |
| 5 | 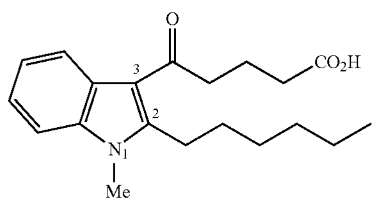 |
| 6 | 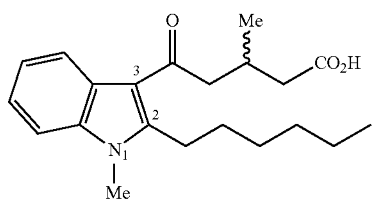 |
| 7 | 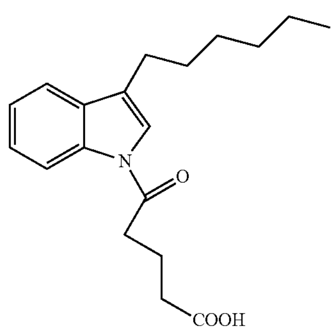 [SMILES: CCCCCCc1cn(C(=O)CCCC(=O)O)c2ccccc12] |
| 8 | 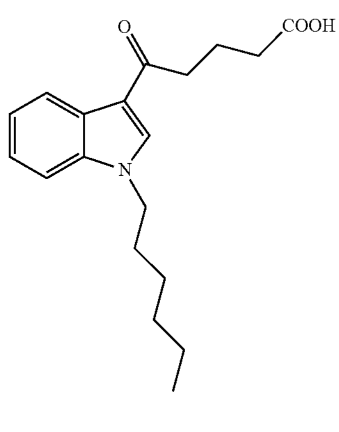 [SMILES: CCCCCCn1cc(C(=O)CCCC(=O)O)c2ccccc21] |

TABLE 1-continued

Representative compounds of the invention

| Compound No. | Structure |
|---|---|
| 10 | 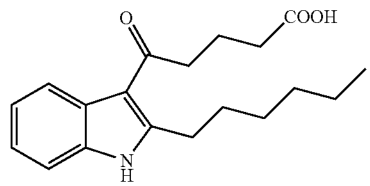 [SMILES: CCCCCCc1[nH]c2ccccc2c1C(=O)CCCC(=O)O] |
| 11 | 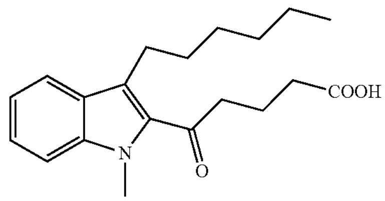 [SMILES: CCCCCCc1c(C(=O)CCCC(=O)O)n(C)c2ccccc12] |
| 12 | 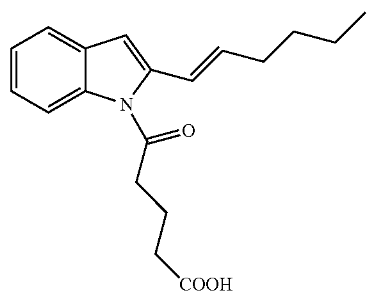 [SMILES: CCCC/C=C/c1cc2ccccc2n1C(=O)CCCC(=O)O] |
| 14 | 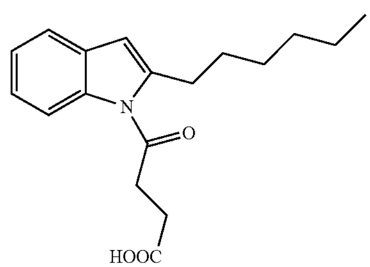 [SMILES: CCCCCCc1cc2ccccc2n1C(=O)CCC(=O)O] |
| 16 | 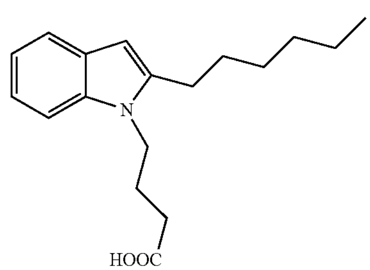 [SMILES: CCCCCCc1cc2ccccc2n1CCCC(=O)O] |
| 17 | 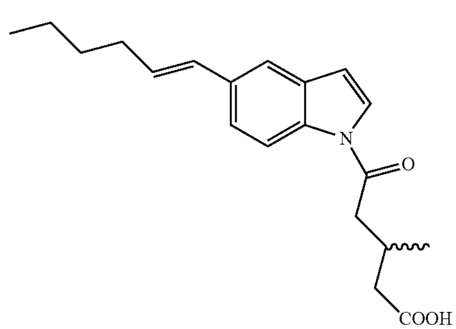 [SMILES: CCCC/C=C/c1ccc2c(ccn2C(=O)CC(C)CC(=O)O)c1] |

TABLE 1-continued
Representative compounds of the invention
| Compound No. | Structure |
|---|---|
| 18 | 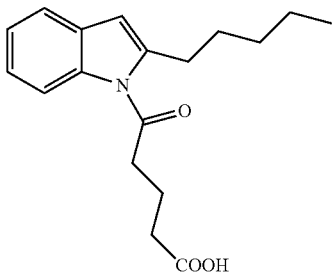 [SMILES: CCCCCc1cc2ccccc2n1C(=O)CCCC(=O)O] |
| 19 | 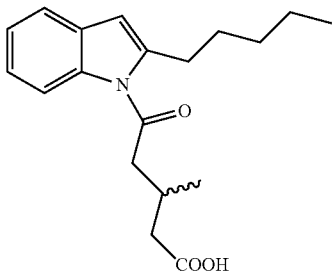 [SMILES: CCCCCc1cc2ccccc2n1C(=O)CC(C)CC(=O)O] |
| 20 | 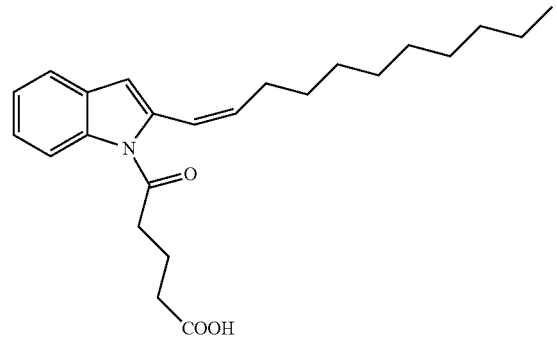 [SMILES: CCCCCCCCC/C=C\c1cc2ccccc2n1C(=O)CCCC(=O)O] |
| 21 | 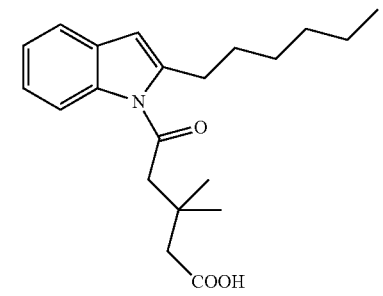 [SMILES: CCCCCCc1cc2ccccc2n1C(=O)CC(C)(C)CC(=O)O] |
| 22 | 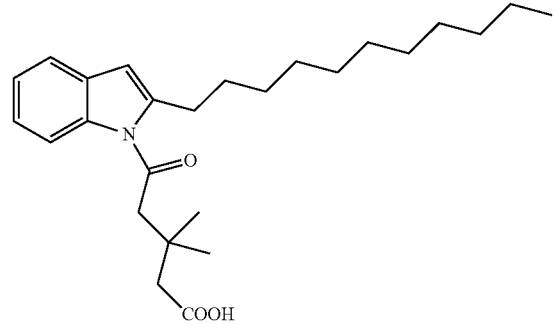 [SMILES: CCCCCCCCCCCc1cc2ccccc2n1C(=O)CC(C)(C)CC(=O)O] |

TABLE 1-continued

Representative compounds of the invention

| Compound No. | Structure |
|---|---|
| 23 | 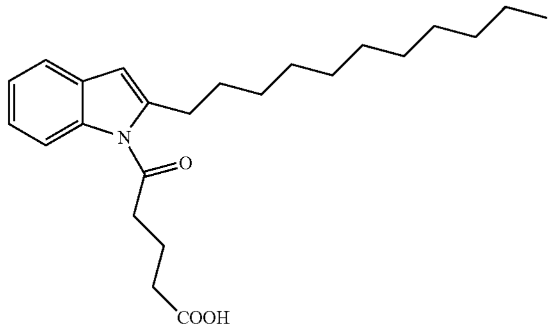 [SMILES: CCCCCCCCCCCc1cc2ccccc2n1C(=O)CCCC(=O)O] |
| 25 | 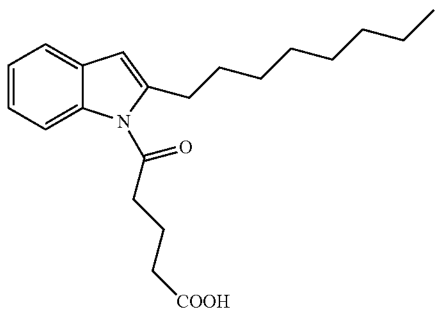 [SMILES: CCCCCCCCc1cc2ccccc2n1C(=O)CCCC(=O)O] |
| 26 | 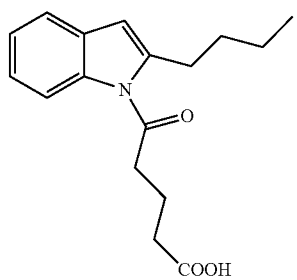 [SMILES: CCCCc1cc2ccccc2n1C(=O)CCCC(=O)O] |
| 27 | 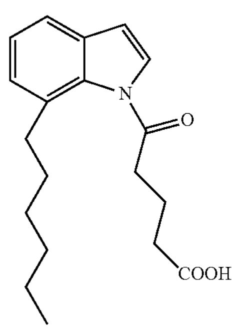 [SMILES: CCCCCCc1cccc2ccn(C(=O)CCCC(=O)O)c12] |
| 28 | 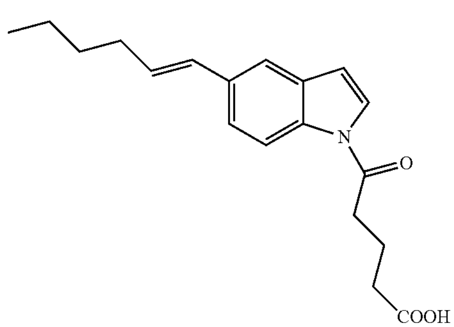 [SMILES: CCCC/C=C/c1ccc2c(ccn2C(=O)CCCC(=O)O)c1] |

TABLE 1-continued
Representative compounds of the invention
| Compound No. | Structure |
|---|---|
| 29 | 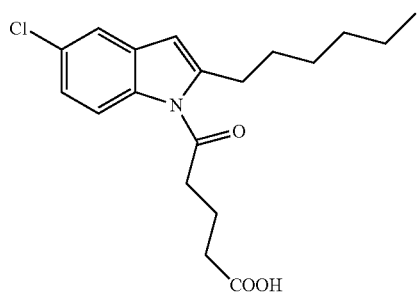 [SMILES: CCCCCCc1cc2cc(Cl)ccc2n1C(=O)CCCC(=O)O] |
| 30 | 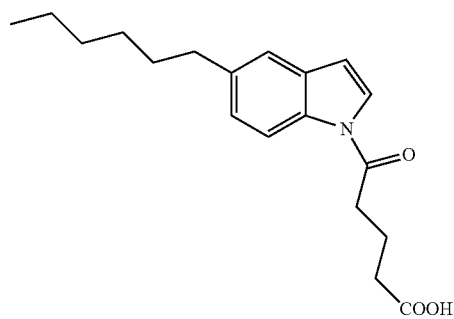 [SMILES: CCCCCCc1ccc2c(ccn2C(=O)CCCC(=O)O)c1] |
| 31 | 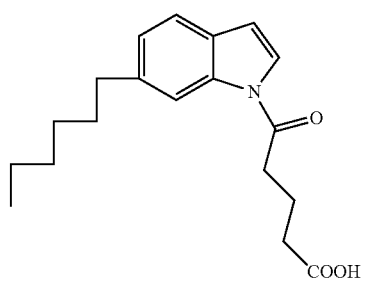 [SMILES: CCCCCCc1ccc2ccn(C(=O)CCCC(=O)O)c2c1] |
| 32 | 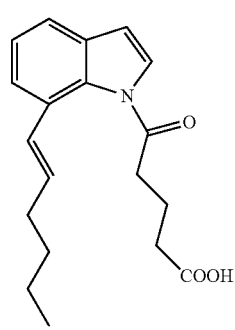 [SMILES: CCCC/C=C/c1cccc2ccn(C(=O)CCCC(=O)O)c12] |
| 33 | 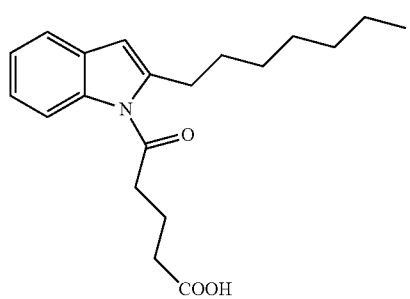 [SMILES: CCCCCCCc1cc2ccccc2n1C(=O)CCCC(=O)O] |

TABLE 1-continued

Representative compounds of the invention

| Compound No. | Structure |
| --- | --- |
| 34 | 2-heptyl-indole with N-C(=O)-CH2-CH(~)-CH2-COOH substituent (stereochemistry undefined) |
| 36 | 5-chloro-2-hexyl-indole with N-C(=O)-CH2-CH(S)(CH3)-CH2-COOH substituent |
| 37 | 2-hexyl-indole with N-C(=O)-CH2-C(cyclopropyl)(CH2COOH) substituent |
| 38 | 2-hexyl-indole with N-C(=O)-CH(CH3)-CH2-CH2-COOH substituent |
| 39 | 2-hexyl-indole with N-C(=O)-CH2-CH2-CH(CH3)-COOH substituent |
| 40 | 2-hexyl-indole with N-C(=O)-(3-carboxyphenyl) substituent |

TABLE 1-continued
Representative compounds of the invention
| Compound No. | Structure |
|---|---|
| 41 | 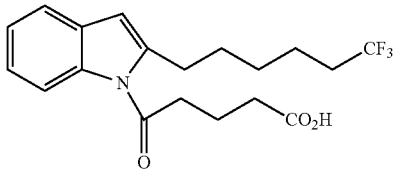 [SMILES: O=C(O)CCCC(=O)n1c(CCCCCC(F)(F)F)cc2ccccc21] |
| 42 | 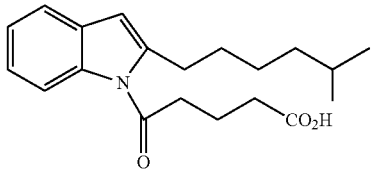 [SMILES: CC(C)CCCCc1cc2ccccc2n1C(=O)CCCC(=O)O] |
| 43 | 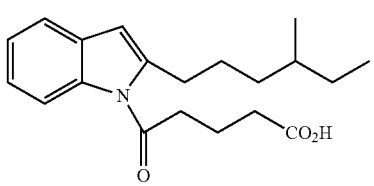 [SMILES: CCC(C)CCCc1cc2ccccc2n1C(=O)CCCC(=O)O] |
| 44 | 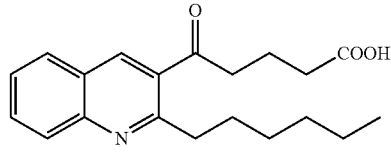 [SMILES: CCCCCCc1nc2ccccc2cc1C(=O)CCCC(=O)O] |
| 45 | 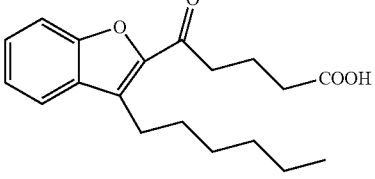 |
| 46 | 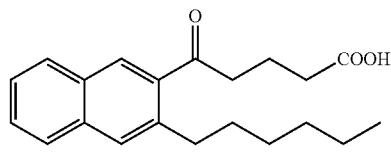 [SMILES: CCCCCCc1cc2ccccc2cc1C(=O)CCCC(=O)O] |
| 47 | 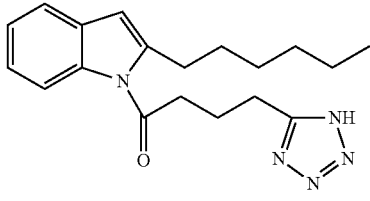 [SMILES: CCCCCCc1cc2ccccc2n1C(=O)CCCc1nnn[nH]1] |
| 48 | 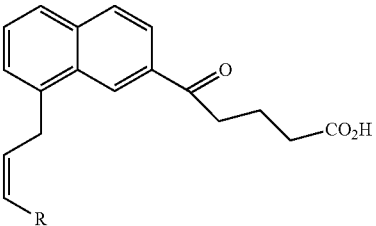 |

TABLE 1-continued
Representative compounds of the invention
| Compound No. | Structure |
|---|---|
| 49 | 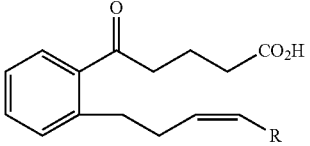 |
| 50 | 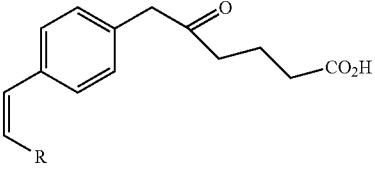 |
| 51 | 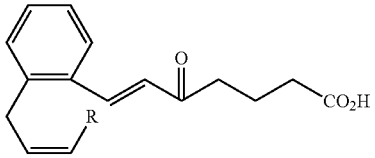 |
| 52 | 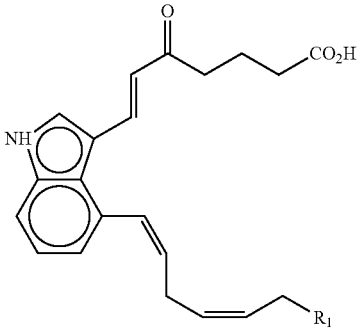 |
| 53 | 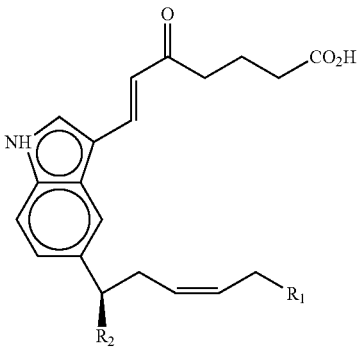 |
| 56 | 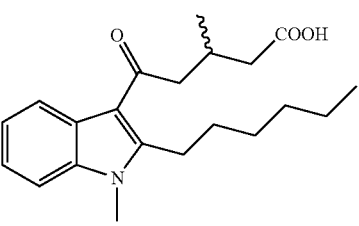 [SMILES: CCCCCCc1c(C(=O)CC(C)CC(=O)O)c2ccccc2n1C] |

TABLE 1-continued
Representative compounds of the invention
| Compound No. | Structure |
|---|---|
| 57 | 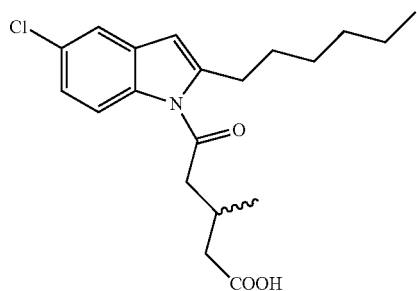 [SMILES: CCCCCCc1cc2cc(Cl)ccc2n1C(=O)CC(C)CC(=O)O] |
| 58 | 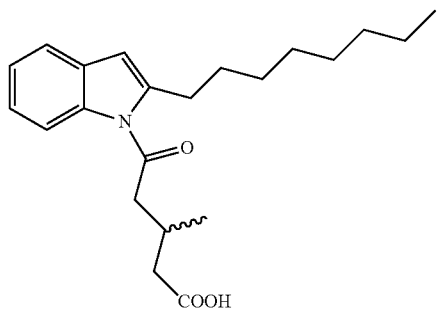 [SMILES: CCCCCCCCc1cc2ccccc2n1C(=O)CC(C)CC(=O)O] |
| 59 | 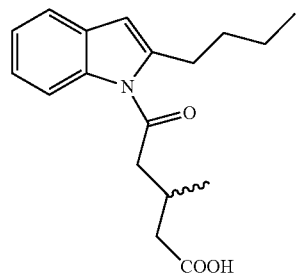 [SMILES: CCCCc1cc2ccccc2n1C(=O)CC(C)CC(=O)O] |
| 60 | 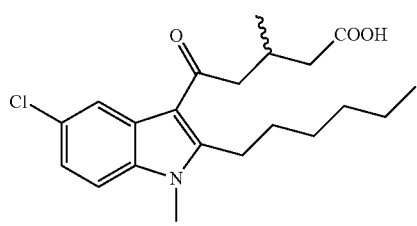 [SMILES: CCCCCCc1c(C(=O)CC(C)CC(=O)O)c2cc(Cl)ccc2n1C] |
| 61 | 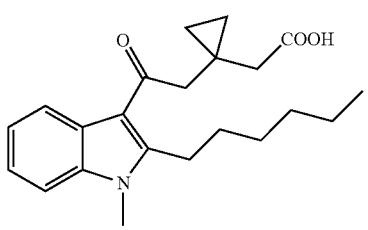 [SMILES: CCCCCCc1c(C(=O)CC2(CC(=O)O)CC2)c2ccccc2n1C] |

TABLE 1-continued

Representative compounds of the invention

| Compound No. | Structure |
|---|---|
| 62 | *(2-pentyl-benzimidazole N-acylated with 3-substituted glutaric acid half structure)* |
| 73 | *(1-pentyl-indol-3-yl acetic acid)* |
| 76 | *(1-pentyl-indol-3-yl acrylic acid, trans)* |
| 77 | *(1-tosyl-indol-3-yl (E)-6-oxohept-1-en-... COOH)* |
| 78 | *(5-bromo-1-methyl-indol-3-yl acrylic acid)* |
| 79 | *(5-(hept-1-yn-1-yl)-1-methyl-indol-3-yl acrylic acid)* |

TABLE 1-continued
Representative compounds of the invention
| Compound No. | Structure |
|---|---|
| 87 | 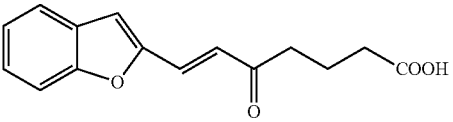 [SMILES: O=C(O)CCCC(=O)/C=C/c1cc2ccccc2o1] |
| 88 | 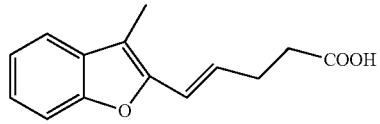 [SMILES: Cc1c(/C=C/CCC(=O)O)oc2ccccc12] |
| 89 | 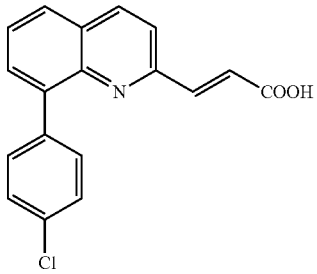 [SMILES: O=C(O)/C=C/c1ccc2cccc(-c3ccc(Cl)cc3)c2n1] |
| 90 | 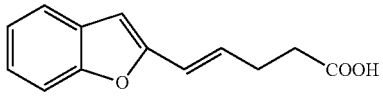 [SMILES: O=C(O)CC/C=C/c1cc2ccccc2o1] |
| 91 | 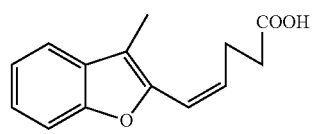 [SMILES: Cc1c(/C=C\CCC(=O)O)oc2ccccc12] |
| 93 | 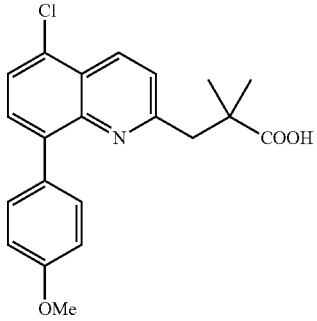 [SMILES: COc1ccc(-c2ccc(Cl)c3ccc(CC(C)(C)C(=O)O)nc23)cc1] |
| 94 | 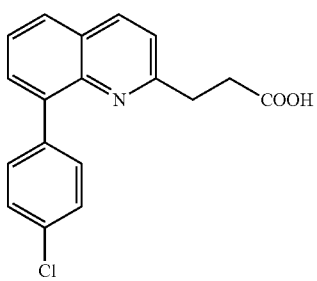 [SMILES: O=C(O)CCc1ccc2cccc(-c3ccc(Cl)cc3)c2n1] |

TABLE 1-continued

Representative compounds of the invention

| Compound No. | Structure |
|---|---|
| 97 | (structure: naphthalene with trans-alkene linked to ketone-CH2-CH2-CH2-COOH) |
| 100 | (structure: 5-chloro-1-methyl-2-hexyl-indole with 3-position acyl group -C(O)-CH2-CH(R)(CH3)-...) |
| 101 | (structure: 5-chloro-1-ethyl-2-hexyl-indole with 3-acyl-CH2-CH(CH2CO2H)- chain) |
| 102 | (structure: 1-ethyl-2-hexyl-indole with 3-acyl-CH2-CH(CH2CO2H)- chain) |
| 103 | (structure: 6-chloro-2-hexyl-indole N-acyl -C(O)-CH2-CH(CH2COOH)-) |
| 104 | (structure: 6-chloro-1-methyl-2-hexyl-indole with 3-acyl-CH2-CH(CH3)-CH2-COOH) |

TABLE 1-continued

Representative compounds of the invention

| Compound No. | Structure |
|---|---|
| 105 | 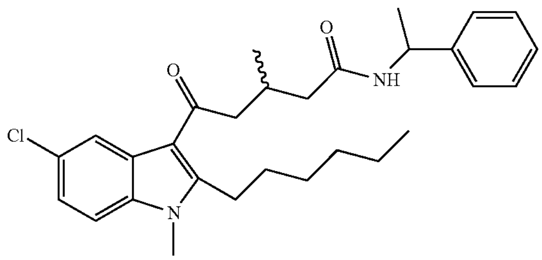 [SMILES: CCCCCCc1c(C(=O)CC(C)CC(=O)NC(C)c2ccccc2)c2cc(Cl)ccc2n1C] |
| 106 | 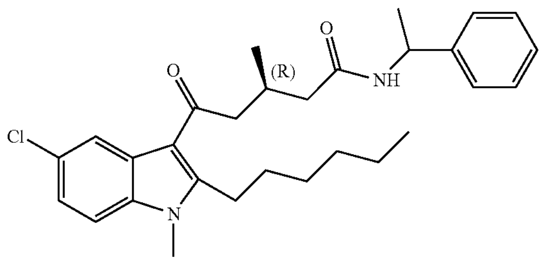 |
| 107 | 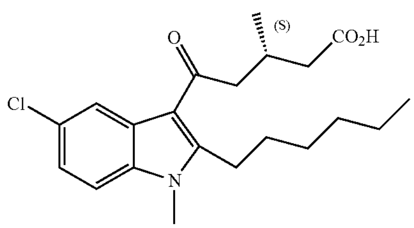 |
| 108 | 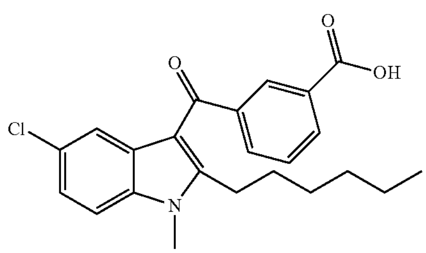 [SMILES: CCCCCCc1c(C(=O)c2cccc(C(=O)O)c2)c2cc(Cl)ccc2n1C] |
| 109 | 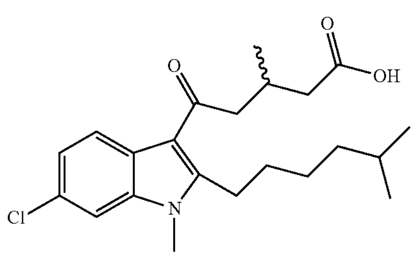 [SMILES: CC(C)CCCCc1c(C(=O)CC(C)CC(=O)O)c2ccc(Cl)cc2n1C] |
| 110 | 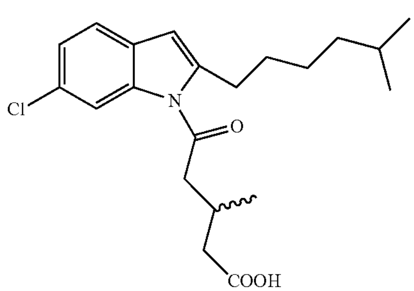 [SMILES: CC(C)CCCCc1cc2ccc(Cl)cc2n1C(=O)CC(C)CC(=O)O] |

TABLE 1-continued

Representative compounds of the invention

| Compound No. | Structure |
|---|---|
| 111 | *(6-chloroindole with hexyl at 2-position, N-acyl with (S)-3-methyl-4-carboxybutanoyl)* |
| 112 | *(6-chloroindole with hexyl at 2-position, N-acyl with (R)-3-methyl-4-carboxybutanoyl)* |
| 113 | *(5-chloro-1-methyl-2-heptylindole, 3-acyl with 3-carboxymethyl-butanoyl)* |
| 114 | *(5-chloro-1-methyl-2-(5-methylhexyl)indole, 3-acyl with 3-carboxymethyl-butanoyl)* |
| 115 | *(5-chloro-2-(5-methylhexyl)indole, N-acyl with 3-carboxymethyl-butanoyl)* |
| 116 | *(6-chloro-2-hexylindole, N-acyl with 3,3-dimethyl-4-carboxybutanoyl)* |
| 117 | *(2-hexylquinoline, 3-acyl with 4-carboxybutanoyl)* |

TABLE 1-continued

Representative compounds of the invention

| Compound No. | Structure |
| --- | --- |
| 118 | (2-pentyl-quinolin-3-yl)-C(=O)-CH₂-CH(~)-CH₂-COOH structure |

It should be understood that references to the compounds of the invention described herein are meant to also include the pharmaceutically acceptable salts as well as acidic and basic forms of the compounds.

Some of the compounds described herein contain one or more centers of asymmetry and may thus give rise to diastereoisomers and optical isomers. The present invention is meant to encompass such possible diastereoisomers as well as their racemic and resolved, optically active forms. Optically active (R) and (S) isomers may be resolved using conventional techniques.

Some of the compounds described herein contain olefinic double bonds, and unless specified otherwise, are meant to include both E and Z geometric isomers.

Pharmaceutical Compositions

The pharmaceutical compositions of the present invention comprise the compounds of the invention described herein, e.g. a compound of Formula I, II, III, IV, V, VI, VII, VIII or IX or a compound of Table 1 or a pharmaceutically acceptable salt thereof, as an active ingredient, and may also contain a pharmaceutically acceptable carrier. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

Any suitable route of administration may be employed for providing a mammal, especially a human with an effective dosage of a compound or composition of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of the invention in suitable propellants, such as fluorocarbons or hydrocarbons.

Suitable topical formulations of the compounds and compositions of the invention include transdermal devices, aerosols, creams, ointments, lotions, dusting powders, and the like.

In practical use, the compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or non-aqueous techniques.

In addition to the common dosage forms set out above, the compounds of the invention may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. For example, in an embodiment each tablet may contain from about 2.5 mg to about 500 mg of the active ingredient and each cachet or capsule may contain from about 2.5 to about 500 mg of the active ingredient.

The magnitude of prophylactic or therapeutic dose of a compound of the invention will, of course, vary with the nature of the severity of the condition to be treated and with the particular compound of the invention and its route of administration. It will also vary according to the age, weight and response of the individual patient. In general, the daily dose range for treating respiratory diseases (which may or may not be associated with inflammation), or for anti-asthmatic, anti-allergic or anti-inflammatory use, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, in an embodiment a suitable dosage range for treating respiratory diseases, or for anti-asthmatic, anti-inflammatory or anti-allergic use, is from about 0.001 mg to about 25 mg (preferably from 0.01 mg to about 1 mg) of a compound of the invention per kg of body weight per day.

In the case where an oral composition is employed, in an embodiment a suitable dosage range for treating respiratory diseases, or for anti-asthmatic, anti-inflammatory or anti-allergic use, is, e.g. from about 0.01 mg to about 100 mg of a compound of the invention per kg of body weight per day, preferably from about 0.1 mg to about 10 mg per kg.

For the treatment of diseases of the eye, ophthalmic preparations for ocular administration comprising 0.001-1% by weight solutions or suspensions of the compounds of the invention in an acceptable ophthalmic formulation may be used in an embodiment.

Methods of Treatment and Medical Uses

Metabolites of arachidonic acid such as 5-oxo-ETE and other eicosanoids are potent chemoattractants for eosinophils and neutrophils both in vitro and in vivo, and stimulate a variety of responses in these cells, such as actin polymerization, calcium mobilization, integrin expression and degranulation (Powell and Rokach, Progress in Lipid Research 44: 154-183 (2005)). 5-Oxo-ETE is also a chemoattractant for monocytes and has been shown to stimulate the proliferation of tumor cells. Through their effects on both cell migration and survival, eicosanoids such as 5-oxo-ETE are involved in the pathogenesis of diseases involving eosinophils, including asthma and other inflammatory diseases. They may also be involved in the growth of cancers, e.g. the progression of tumors, e.g. tumors of the prostate. Accordingly the compounds and compositions provided herein are useful for the therapy or prophylaxis of eosinophilic and inflammatory conditions. In some embodiments, the compounds and compositions of the invention are useful for the therapy or prophylaxis of cancer, e.g. prostate cancer.

There are many diseases or conditions that are inflammatory in their nature. For example, inflammatory diseases that affect the population include asthma, allergic rhinitis, chronic obstructive pulmonary disease, idiopathic pulmonary fibrosis, and rhinitis. Inflammation is also a common cause of pain. Inflammatory pain may arise for numerous reasons, such as infection, surgery or other trauma. The term "inflammation" will be understood by those skilled in the art to include any condition characterised by a localised or a systemic protective response, which may be elicited by physical trauma, infection, chronic diseases, such as those mentioned hereinbefore, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white blood cells, loss of function and/or any other symptoms known to be associated with inflammatory conditions. The term "inflammation" will thus also be understood to include any inflammatory disease, disorder or condition per se, any condition that has an inflammatory component associated with it, and/or any condition characterised by inflammation as a symptom, insofar as it is related to a respiratory disease or condition, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Accordingly, compounds and compositions of the invention may be used in the treatment or prevention of inflammation. In an aspect, the compounds and compositions of the invention are used in the treatment or prevention of respiratory conditions, asthma, chronic obstructive pulmonary disease, pulmonary fibrosis, inflammatory pain, fever, viral infections (e.g. influenza, common cold), allergic rhinitis, allergic disorders, rhinitis, and any other respiratory disease with an inflammatory component, characterized by inflammation or characterized by eosinophilia. It is also contemplated that the compounds and compositions of the invention are used in the treatment or prevention of cancer, for example prostate cancer.

Asthma is a common chronic disorder of the airways that is complex and characterized by variable and recurring symptoms including airflow obstruction, bronchoconstriction and an underlying inflammation. Treatment regimens for asthma vary depending on the severity of the condition. As used herein, the term "asthma" includes all types of asthma, including without limitation: mild, moderate and severe asthma; exercise-induced asthma; aspirin-induced asthma; extrinsic or allergic asthma; intrinsic or non-allergic asthma;

occupational asthma; cough-variant asthma; nocturnal asthma; child-onset asthma; and adult-onset asthma.

Another common disease of the airways with inflammatory and bronchoconstrictive components is chronic obstructive pulmonary disease (COPD). COPD refers to a group of diseases of the lungs in which the airways become narrowed, typically due to an abnormal inflammatory response in the lungs. Non-limiting examples of COPD include bronchitis and emphysema. Idiopathic pulmonary fibrosis (IPF) is another lung disease also involving eicosanoids.

Allergic rhinitis is an inflammation of the nasal passages, usually associated with watery nasal discharge and itching of the nose and eyes. Allergies occur when the immune system overreacts to particles in the air and produces an allergic reaction.

Compounds and compositions of the invention are indicated both in the therapeutic and/or prophylactic treatment of the diseases and conditions discussed herein. Accordingly, in an aspect of the present invention, there is provided a method of treatment or prevention of inflammation or of a respiratory disease or condition associated with inflammation, which method comprises administration of a compound or composition of the invention to a subject. In accordance with another aspect, there is provided a method of treatment or prevention of a disease by inhibition of eicosanoids such as 5-oxo-ETE and 5-HETE, which method comprises administration of a compound or composition of the invention to a subject. According to another aspect of the present invention, there is provided a method of inhibiting eicosanoids such as 5-oxo-ETE and 5-HETE and/or the 5-oxo-ETE receptors, such as the OXE receptor, which method comprises administration of a compound or composition of the invention to a subject. In another aspect, respiratory diseases or conditions which are not associated with inflammation are treated or prevented by administration of the compounds and/or compositions disclosed herein to a subject.

It should be understood that, in addition to blocking biological responses to 5-oxo-ETE and 5-HETE, the compounds and compositions of the invention may block biological responses to other related eicosanoids which can also act as ligands for the OXE receptor. Thus "eicosanoid", as used herein, means a substance derived from a fatty acid having 20 carbon atoms, such as eicosanoic acid, and in an aspect, a fatty acid in which the 8th position is unsaturated. Non-limiting examples of eicosanoids which are encompassed in the methods presented herein include 5-oxo-ETE, 5-HETE, 5-HPETE, arachidonic acid, 5-oxo-ETrE (5-oxo-6E,8Z,11Z-eicosatrienoic acid), 5-HETrE (5-hydroxy-6E,8Z,11Z-eicosatrienoic acid), eicosa-5Z, 8Z, 11Z-trienoic acid, 5-oxo-EDE (5-oxo-6E,8Z-eicosadienoic acid), and eicosa-5Z,8Z-dienoic acid. In addition, certain 18-carbon polyunsaturated fatty acids are included, e.g. 5-oxo-ODE (5-oxo-6E,8Z-octadecadienoic acid), 5-HODE (5-hydroxy-6E,8Z-octadecadienoic acid), and sebaleic acid (5Z,8Z-octadecadienoic acid).

In yet another aspect of the present invention there is provided a method of treatment or prevention of a respiratory disease, which method comprises administration of a compound or composition of the invention to a subject. In a further aspect of the present invention, there is provided a method of treatment or prevention of asthma, which method comprises administration of a compound or composition of the invention to a subject.

In another aspect, there is provided a method of treatment or prevention of an inflammatory disease, which method comprises administration of a compound or composition of the invention to a subject, wherein the inflammatory disease is selected from the group consisting of asthma, allergic rhinitis, COPD, and idiopathic pulmonary fibrosis. As mentioned above, eicosanoids acting through the OXE receptor mediate migration of eosinophils and neutrophils. In yet another aspect therefore, there is provided a method for inhibiting migration of eosinophils and neutrophils, comprising administration of a compound or composition of the invention to a subject. Treatment or prevention of disease states which are expected to be alleviated by inhibition of eosinophil or neutrophil migration is also encompassed.

It has been shown that 5-oxo-ETE can stimulate proliferation of prostate tumor cells and the OXE receptor is expressed on prostate tumor cells. Metabolites of arachidonic acid including HETEs and oxo-ETEs have been shown to increase growth and promote survival of a variety of cancers, including lung, pancreatic and prostate cancer. Moreover 5-hydroxyeicosatetraenoids are the principal arachidonic acid metabolite in prostate cancer cells (see e.g. WO 2007/025254 and US 2005/0106603 for review of the role of G-protein coupled eicosanoid receptors in cancer). These findings indicate a role for the 5-oxo-ETE receptor antagonists of the present invention in treatment or prevention of prostate cancer, as well as induction of apoptosis in prostate cancer cells.

Thus in an embodiment, the compounds and compositions presented herein are used for the treatment or prevention of cancer, including lung, pancreatic and/or prostate cancer. In an aspect, there is provided herein a method of treatment or prevention of prostate cancer, which method comprises administration of a compound or composition of the invention to a subject, e.g. a human subject in need thereof. In another aspect, there is provided a method for inducing apoptosis in a cancer cell, e.g. a prostate cancer cell, comprising administration of a compound or composition of the invention to a subject.

As used herein, "subject" includes mammals, including humans.

In an embodiment, the methods disclosed herein comprise administration of a therapeutically effective amount of a compound or composition of the invention, to a subject in need thereof. A subject "in need thereof" is a subject suffering from or susceptible to the disease or condition in question. The term "therapeutically effective amount" refers to an amount of a compound which confers a therapeutic effect on the treated subject. The effect may be objective (i.e. measurable by some test or marker) or subjective (i.e. the subject gives an indication of or feels an effect). The term "effective amount" refers to an amount of a compound which is sufficient to produce the desired result or has the desired biological effect.

Use of the compounds of the invention in the manufacture of a medicament for treating the diseases disclosed herein are also encompassed, as are compositions for use for treating or preventing the described diseases.

Combinations with other Therapeutic Agents

In the methods and uses of the present invention the compounds of the invention can also be administered concomitantly with other therapeutic agents. In an embodiment, the present invention provides a method of preventing or treating inflammatory conditions, e.g. asthma, allergies, COPD, etc., that includes concomitantly administering to a subject in need thereof an effective amount of a first agent comprising the compounds and compositions of the invention, and a second agent.

The second agent may be, for example, an agent having analgesic, anti-inflammatory and/or anti-allergic properties. Non-limiting examples of second agents contemplated for use in the methods of the invention include: cyclooxygenase inhibitors, non-steroidal anti-inflammatory drugs (NSAIDs) such as acetyl salicylic acid, ibuprofen and naproxen, and peripheral analgesic agents. Compounds and pharmaceutical compositions comprising the compounds of the invention may also be used in combination with leukotriene modifiers, e.g. inhibitors of the biosynthesis of the leukotrienes, such as zileuton (Zyflo®), and leukotriene antagonists such as montelukast (Singulair®) and zafirlukast (Accolate®). Other types of agents which may be useful in combination with the compounds of the present invention include anti-cholinergics, bronchodilators, corticosteroids, beta-2 agonists and other anti-asthmatic drugs such as calcium antagonists.

Concomitant administration includes co-administration (simultaneous administration of a first and second agent) and sequential administration (administration of a first agent, followed by the second agent, or administration of the second agent, followed by the first agent). The combination of agents used within the methods described herein may have a therapeutic additive or synergistic effect on the condition(s) or disease(s) targeted for treatment. The combination of agents used within the methods described herein also may reduce a detrimental effect associated with at least one of the agents when administered alone or without the other agent(s). For example, the toxicity of side effects of one agent may be attenuated by the other, thus allowing a higher dosage, improving patient compliance, or improving therapeutic outcome. Physicians may achieve the clinical benefits of previously recognized drugs while using lower dosage levels, thus minimizing adverse side effects. In addition, two agents administered simultaneously and acting on different targets may act synergistically to modify or ameliorate disease progression or symptoms.

Examples of NSAIDs which may be co-administered include, but are not limited to: acetyl salicylic acid, amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, diclofenac, di-fisalamine, difenpyramide, emorfazone, enfenamic acid, enolioam, epirizole, etersalate, etodolac, etofenamate, fanetizole mesylate, fenclorac, fenbufen, fenoprofen, flurbiprofen, fendosal, fenflumizole, feprazone, floctafenine, flunixin, flunoxaprofen, fluproquazone, fopirtoline, fosfosal, furcloprofen, glucametacin, guaimesal, ibuprofen, ibuproxam, indomethacin, isofezolac, isonixim, isoprofen, isoxicam, ketoprofen, lefetamine HCl, leflunomide, lofemizole, lonazolac calcium, lotifazole, loxoprofen, lysin clonixinate, meclofenamate sodium, meseclazone, nabumetone, nictindole, nimesulide, naproxen, phenylbutazone, piroxicam, sulindac, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolmetin, tolpadol, tryptamid and ufenamate.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Methods of Synthesis

Compounds of the invention can be prepared according to the synthetic routes outlined below and by following the methods described herein.

For example, compounds having the following structure, wherein the substituents are as described, may be made according to the scheme shown:

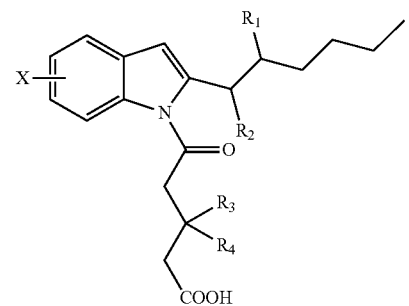

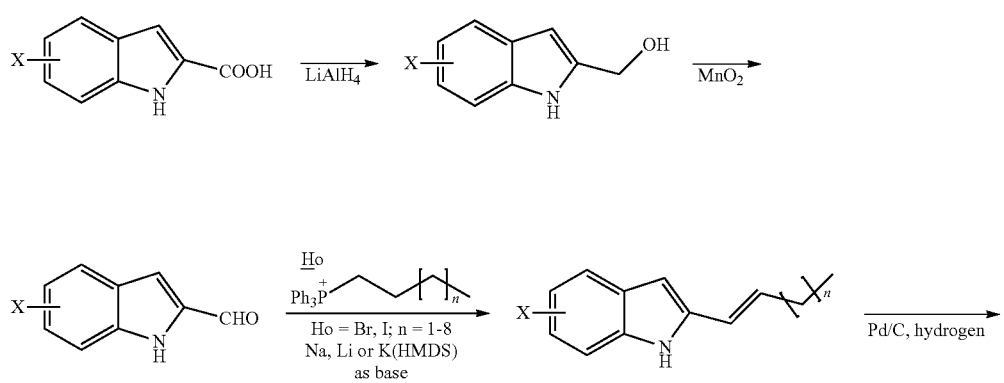

-continued
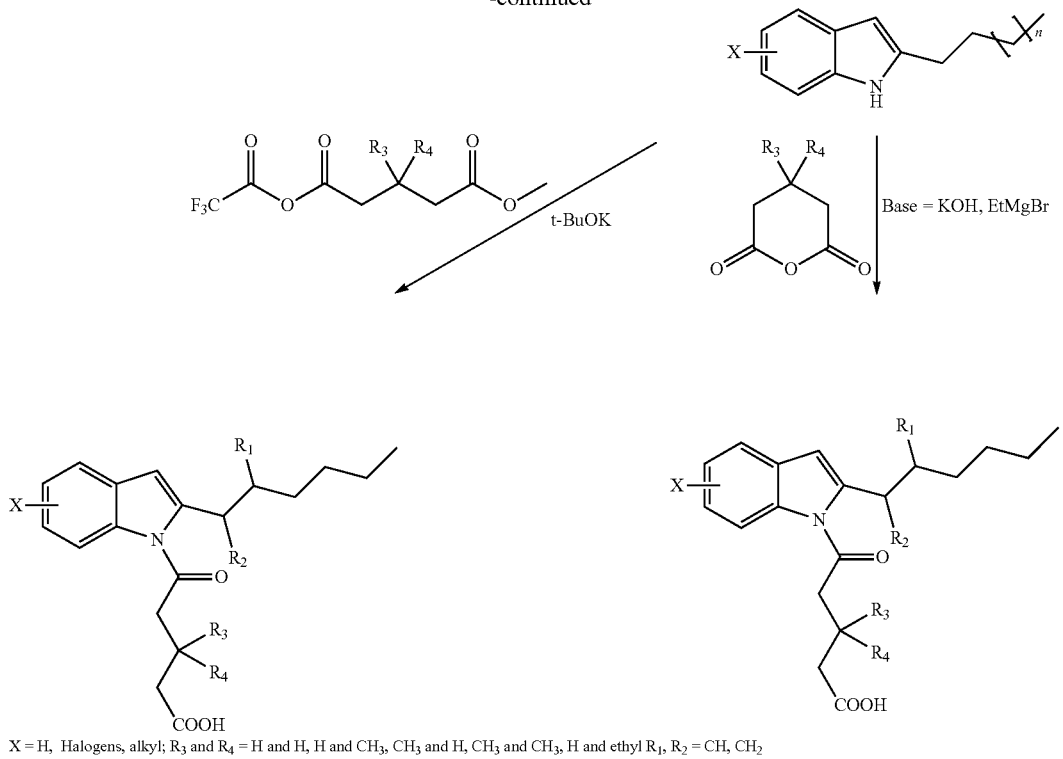
X = H, Halogens, alkyl; R₃ and R₄ = H and H, H and CH₃, CH₃ and H, CH₃ and CH₃, H and ethyl R₁, R₂ = CH, CH₂
In another example, compounds having the following structure, wherein the substituents are as described, may be made according to the scheme shown:
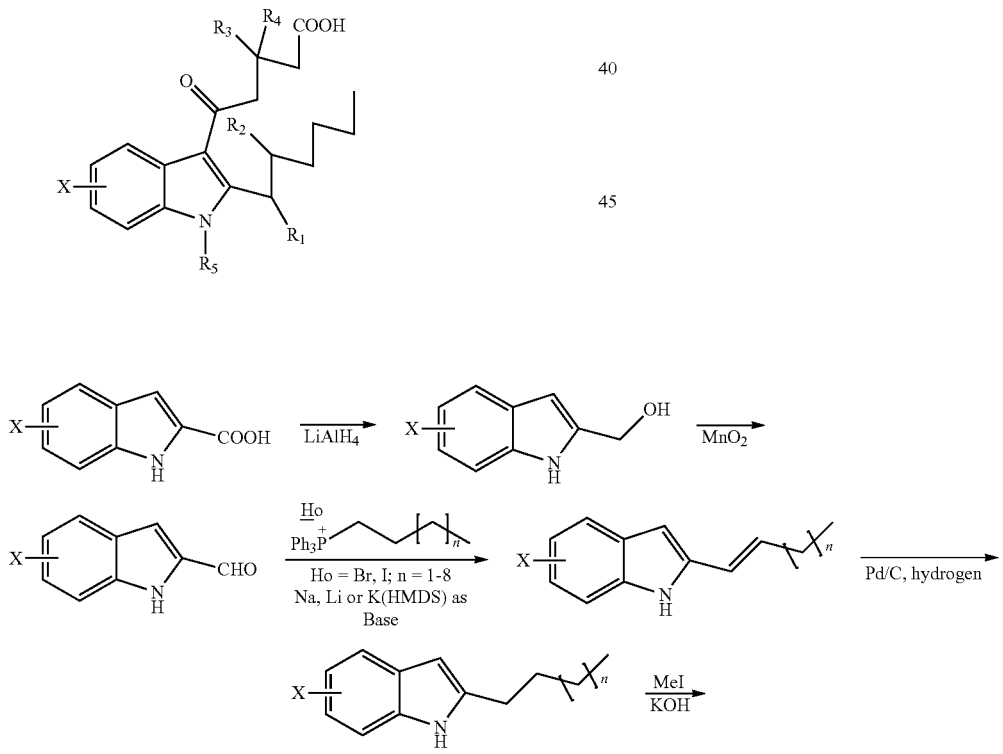

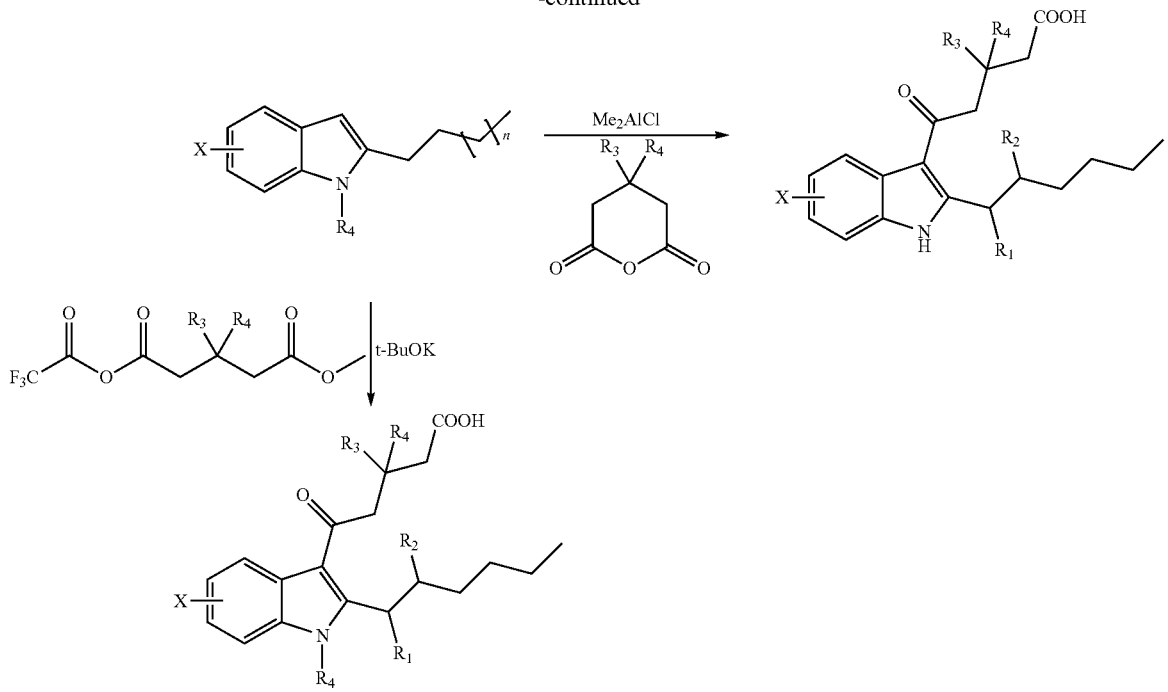

X = H, Halogens, alkyl; $R_3$ and $R_4$ = H and H, H and $CH_3$, $CH_3$ and H, $CH_3$ and $CH_3$, H and ethyl
$R_1$, $R_2$ = CH, $CH_2$; $R_5$ = H, $CH_3$, $CH_2CH_3$

Example 1

Compound #12 (5-(2-Hex-1-enyl-indol-1-yl)-5-oxo-pentanoic acid) was prepared using the following procedure:

Step 1 (2-Hex-1-enyl-1H-indole)

To a suspension of pentyl-triphenyl-phosphonium bromide in THF was added LiHMDS in THF and the mixture was stirred for 30 minutes. A solution of 1H-indole-2-carbaldehyde in THF was added to the reaction mixture and stirred for 3 hours. The reaction was treated with saturated ammonium chloride and ethyl acetate. The product was purified by column chromatography.

Step 2 (5-(2-Hex-1-enyl-indol-1-yl)-5-oxo-pentanoic acid)

To a solution of 2-hex-1-enyl-1H-indole in DMSO was added KOH at RT and this was stirred for 30 minutes. Dihydro-pyran-2,6-dione was added to the reaction mixture and stirred for 3 hours. The reaction was treated with saturated ammonium chloride and ethyl acetate. The product was purified by column chromatography.

Example 2

Compound #17 (5-(5-Hex-1-enyl-indol-1-yl)-3-methyl-5-oxo-pentanoic acid) was prepared by using the same procedure as for compound #12 using 1H-indole-5-carbaldehyde in step 1 and 4-methyl-dihydro-pyran-2,6-dione in step 2.

Example 3

Compound #1 (5-(2-Hexyl-indol-1-yl)-5-oxo-pentanoic acid) was prepared using the following procedure:

Step 1

To a suspension of pentyl-triphenyl-phosphonium bromide in THF was added LiHMDS in THF and the mixture was stirred for 30 minutes. The solution of 1H-indole-2-carbaldehyde in THF was added to the reaction mixture and stirred for 3 hours. The reaction was treated with saturated ammonium chloride and ethyl acetate. The product was purified by column chromatography.

Step 2 (2-Hexyl-1H-indole)

2-Hex-1-enyl-1H-indole was dissolved in ethanol and 10% palladium on carbon was added to the solution. The reaction flask was sealed and exposed to hydrogen gas under pressure until the hydrogen gas consumption was stopped completely. The reaction mixture was filtered through Celite. The solvent was evaporated to afford the product.

Step 3 (5-(2-Hexyl-indol-1-yl)-5-oxo-pentanoic acid)

To a solution of 2-hexyl-1H-indole in DMSO was added KOH at RT and was stirred for 30 minutes. Then to this mixture dihydro-pyran-2,6-dione was added and stirred for 3 hours. The reaction was treated with saturated ammonium chloride and ethyl acetate. The product was purified by column chromatography.

Example 4

Compound #7 (5-(3-Hexyl-indol-1-yl)-5-oxo-pentanoic acid) was prepared similarly using the same procedure as described above for compound #1 using 1H-indole-3-carbaldehyde in step 1.

Example 5

Compound #18 (5-Oxo-5-(2-pentyl-indol-1-yl)-pentanoic acid) was prepared similarly using the same procedure as described above for compound #1 by using butyl-triphenyl-phosphonium bromide in step 1.

Example 6

Compound #14 (4-(2-Hexyl-indol-1-yl)-4-oxo-butyric acid) was prepared similarly using the same procedure as described above for compound #1 by using dihydro-furan-2,5-dione in step 3.

Example 7

Compound #16 (4-(2-Hexyl-indol-1-yl)-butyric acid) was prepared similarly using the same procedure as described above for compound #1 but by using dihydro-furan-2-one in step 3.

Example 8

Compound #2 (5-(2-Hexyl-indol-1-yl)-3-methyl-5-oxo-pentanoic acid) was prepared using the following procedure:

Step 1 (2-Hex-1-enyl-1H-indole)

To a suspension of pentyl-triphenyl-phosphonium bromide in THF was added LiHMDS in THF and the mixture was stirred for 30 minutes, A solution of 1H-indole-2-carbaldehyde in THF was added to the reaction mixture and stirred for 3 hours. The reaction was treated with saturated ammonium chloride and ethyl acetate. The product was purified by column chromatography.

Step 2 (2-Hexyl-1H-indole)

2-hex-1-enyl-1H-indole was dissolved in ethanol and 10% palladium on carbon was added to the solution. The reaction flask was sealed and exposed to hydrogen gas under pressure until the hydrogen gas consumption was stopped completely. The reaction mixture was filtered through Celite. The solvent was evaporated to afford the product.

Step 3 (5-(2-Hexyl-indol-1-yl)-3-methyl-5-oxo-pentanoic acid)

To a solution of 2-hexyl-1H-indole in DMSO was added KOH at RT and was stirred for 30 minutes. Then to this mixture, 4-methyl-dihydro-pyran-2,6-dione was added and stirred for 3 hours. The reaction was treated with saturated ammonium chloride and ethyl acetate. The product was purified by column chromatography.

Example 9

Compound #19 (3-Methyl-5-oxo-5-(2-pentyl-indol-1-yl)-pentanoic acid) was prepared similarly as described above for compound #2 by using butyl-triphenyl-phosphonium bromide in step 1.

Example 10

Compound #37 ({1-[2-(2-Hexyl-indol-1-yl)-2-oxo-ethyl]-cyclopropyl}-acetic acid) was prepared similarly as described above for compound #2 by using 6-Oxa-spiro[2.5]octane-5,7-dione in step 3.

Example 11

Compound #8 (5-(1-Hexyl-1H-indol-3-yl)-5-oxo-pentanoic acid) was prepared using the following procedure:

Step 1 (1-Hexyl-1H-indole)

To a solution of 1H-indole in DMSO was added KOH at RT and was stirred for 30 minutes. Then to this mixture, 1-bromo-hexane was added and stirred for 3 hours. The reaction was treated with saturated ammonium chloride and ethyl acetate. The product was purified by column chromatography.

Step 2 (5-(1-Hexyl-1H-indol-3-yl)-5-oxo-pentanoic acid methyl ester)

To a solution of 1-hexyl-1H-indole in methylene chloride at 0° C. was added dimethyl aluminum chloride solution in hexane. The reaction mixture was stirred for 30 minutes. To the above reaction mixture was added 4-chlorocarbonyl-butyric acid methyl ester at 0° C. and the reaction mixture was stirred for 3 hours. The reaction was treated with saturated ammonium chloride and ethyl acetate. The product was purified by column chromatography.

Step 3

To a solution of 5-(1-hexyl-1H-indol-3-yl)-5-oxo-pentanoic acid methyl ester in isopropanol and water was added LiOH and stirred for 3 hours. The reaction was treated by 1M HCL and ethyl acetate. The product was purified by column chromatography.

Example 12

Compound #11 (5-(3-Hexyl-1-methyl-1H-indol-2-yl)-5-oxo-pentanoic acid) was prepared using the following procedure:

Step 1 (3-Hex-1-enyl-1H-indole)

To a suspension of pentyl-triphenyl-phosphonium bromide in THF was added LiHMDS in THF and the mixture was stirred for 30 minutes. A solution of 1H-indole-3-carbaldehyde in THF was added to the reaction mixture and stirred for 3 hours. The reaction was treated with saturated ammonium chloride and ethyl acetate. The product was purified by column chromatography.

Step 2 (3-Hexyl-1H-indole)

3-Hex-1-enyl-1H-indole was dissolved in ethanol and 10% palladium on carbon was added to the solution. The reaction flask was sealed and exposed to hydrogen gas under pressure and was stirred until the hydrogen gas consumption was completely stopped. The reaction mixture was filtered through celite. The solvent was evaporated to afford the product.

Step 3 (3-Hexyl-1-methyl-1H-indole)

To a solution of 3-hexyl-1H-Indole in DMSO was added KOH at RT and was stirred for 30 minutes. Iodomethane was added to the above mixture and stirred for 3 hours. The reaction was treated with saturated ammonium chloride and ethyl acetate. The product was purified by column chromatography.

Step 4 (5-(3-Hexyl-1-methyl-1H-indol-2-yl)-5-oxo-pentanoic acid methyl ester)

To a solution of 3-hexyl-1-methyl-1H-indole in methylene chloride at 0° C. was added dimethyl aluminum chloride solution in hexane. The reaction mixture was stirred for 30 minutes. To this solution 4-chlorocarbonyl-butyric acid methyl ester was added at 0 ° C. and the reaction mixture was stirred for 3 hours. The reaction was treated with saturated ammonium chloride and ethyl acetate. The product was purified by column chromatography.

Step 5 (5-(3-Hexyl-1-methyl-1H-indol-2-yl)-5-oxo-pentanoic acid)

To a solution of 5-(3-hexyl-1-methyl-1H-indol-2-yl)-5-oxo-pentanoic acid methyl ester in isopropanol and water was added LiOH and stirred for 3 hours. The reaction was treated with 1M HCL and ethyl acetate. The product was purified by column chromatography.

Example 13

Compound #3 (5-(2-Hexyl-indol-1-yl)-3(R)-methyl-5-oxo-pentanoic acid) was prepared using the following procedure:

Step 1 (2-Hex-1-enyl-1H-indole)

To a suspension of pentyl-triphenyl-phosphonium bromide in THF was added
LiHMDS in THF and the mixture was stirred for 30 minutes. A solution of 1H-indole-2-carbaldehyde in THF was added to the reaction mixture and stirred for 3 hours. The reaction was treated with saturated ammonium chloride and ethyl acetate. The product was purified by column chromatography.

Step 2 (2-Hexyl-1H-indole)

2-Hex-1-enyl-1H-indole was dissolved in ethanol and 10% palladium on carbon was added to the solution. The reaction flask was sealed and exposed to hydrogen gas under pressure and was stirred until the hydrogen gas consumption was completely stopped. The reaction mixture was filtered through Celite. The solvent was evaporated to afford the product.

Step 3 (5-(2-Hexyl-indol-1-yl)-3-methyl-5-oxo-pentanoic acid methyl ester)

In flask A postassium-tert-butoxide solution in THF was added to a solution of 2-hexyl-1H-indole and stirred for 30 minutes. In another flask B trifluoro acetic anhydride was added to a solution of 3(R)-methyl-pentanedioic acid monomethyl ester in methylene chloride and stirred for 20 minutes. The solution in flask A was transferred to solution in flask B and the reaction mixture was stirred for 3 hours. The reaction was treated with saturated ammonium chloride and ethyl acetate. The product was purified by column chromatography.

Step 4 (5-(2-Hexyl-indol-1-yl)-3(R)-methyl-5-oxo-pentanoic acid)

To a solution of 5-(2-hexyl-indol-1-yl)-3-methyl-5-oxo-pentanoic acid methyl ester in hexane and buffer was added lipase and was stirred for 24 hours. The reaction mixture was treated with saturated ammonium chloride and ethyl acetate. The product was purified by column chromatography.

Example 14

Compound #4 (5-(2-Hexyl-indol-1-yl)-3(S)-methyl-5-oxo-pentanoic acid) was prepared by using the same procedure as described above for compound #3 but in step 3, 3(S)-methyl-pentanedioic acid monomethyl ester was used in flask B.

Example 15

Compound #20 (5-Oxo-5-(2-undec-1-enyl-indol-1-yl)-pentanoic acid) was prepared using the following procedure:

Step 1 (2-Undec-1-enyl-1H-indole)

To a suspension of decyl-triphenyl-phosphonium bromide in THF was added NaHMDS in THF and the mixture was stirred for 30 minutes. A solution of 1H-indole-2-carbaldehyde was added to the reaction mixture and stirred for 3 hours. The reaction mixture was treated with saturated ammonium chloride and ethyl acetate. The product was purified by column chromatography.

Step 2 (5-Oxo-5-(2-undec-1-enyl-indol-1-yl)-pentanoic acid)

To a solution of 2-undecyl-1H-indole in DMSO was added KOH at RT and was stirred for 30 minutes. To this mixture was added dihydro-pyran-2,6-dione and stirred for 3 hours. The reaction mixture was treated with saturated ammonium chloride and ethyl acetate. The product was purified by column chromatography.

Compound #32 (5-(7-Hex-1-enyl-indol-1-yl)-5-oxo-pentanoic acid) was prepared using the same procedure as described above for compound #20 by using 1H-indole-7-carbaldehyde, pentyl-triphenyl-phosphonium bromide and LIHMDS in step 1.

Compound #28 (5-(5-hex-1-enyl-indol-1-yl)-5-oxo-pentanoic acid) was prepared using the same procedure as described above for compound #20 by using 1H-indole-5-carbaldehyde and pentyl-triphenyl-phosphonium bromide with LIHMDS in step 1.

Example 16

Compound #23 (5-Oxo-5-(2-undecyl-indol-1-yl)-pentanoic acid) was prepared using the following procedure:

Step 1 (2-Undec-1-enyl-1H-indole)

The same procedure as step 1 for compound #20 was used.

Step 2 (2-undecyl-1H-indole)

2-Undec-1-enyl-1H-indole was dissolved in ethanol and 10% palladium on carbon was added to the solution. The reaction flask was sealed and exposed to hydrogen gas under pressure and was stirred until the hydrogen gas consumption was completely stopped. The reaction mixture was filtered through celite. The solvent was evaporated to afford the desired product.

Step 3 (5-Oxo-5-(2-undecyl-indol-1-yl)-pentanoic acid)

To a solution of 2-undecyl-1H-indole in DMSO was added KOH at RT and was stirred for 30 minutes. Then to this mixture was dihydro-pyran-2,6-dione and stirred for 3 hours. The reaction mixture was treated with saturated ammonium chloride and ethyl acetate. The product was purified by column chromatography.

Example 17

Compound #22 (3,3-Dimethyl-5-oxo-5-(2-undecyl-indol-1-yl)-pentanoic acid) was prepared by the same procedure as described above for compound #23 by using 4,4-dimethyldihydro-2H-pyran-2,6(3H)-dione in step 3.

Example 18

Compound #25 (5-(2-Octyl-indol-1-yl)-5-oxo-pentanoic acid) was prepared using the same procedure as described above for compound #23 but in step 1 heptyl tripheyl hosponium iodide was used.

Example 19

Compound #26 (5-(2-Butyl-indol-1-yl)-5-oxo-pentanoic acid) was prepared using the same procedure as described above for compound #23 but in step 1 propyl-tripheyl-phosponium iodide was used.

Example 20

Compound #33 (5-(2-Heptyl-indol-1-yl)-5-oxo-pentanoic acid) was prepared using the same procedure as described above for compound #23 by using hexyl-tripheyl-phosponium iodide in step 1.

Example 21

Compound #27 (5-(7-Hexyl-indol-1-yl)-5-oxo-pentanoic acid) was prepared using same procedure as described above for compound #23 by using pentyl-tripheyl-phosponium bromide and 1H-indole-7-carbaldehyde in step 1.

Example 22

Compound #30 (5-(5-Hexyl-indol-1-yl)-5-oxo-pentanoic acid) was prepared using the same procedure as described above for compound #23 by using pentyl-tripheyl-phosponium bromide and 1H-indole-5-carbaldehyde in step 1.

Example 23

Compound #29 (5-(5-Chloro-2-hexyl-indol-1-yl)-5-oxo-pentanoic acid) was prepared using the same procedure as described above for compound #23 by using 1 pentyl-tripheyl-phosponium bromide and 5-chloro-1H-indole-2-carbaldehyde in step 1.

Example 24

Compound #31 (5-(6-Hexyl-indol-1-yl)-5-oxo-pentanoic acid) was prepared using the same procedure as described above for compound #23 by using pentyl-tripheyl-phosponium bromide and 1H-indole-6-carbaldehyde in step 1.

Example 25

Compound #5 (5-(2-Hexyl-1-methyl-1H-indol-3-yl)-5-oxo-pentanoic acid) was prepared using the following procedure:

Step 1 (2-Hex-1-enyl-1H-indole)

Same procedure as described for compound #20 by using pentyl-triphenyl-phosphonium bromide.

Step 2 (2-Hexyl-1H-indole)

2-hexyl-1H-indole was dissolved in ethanol and 10% palladium on carbon was added to the solution. The reaction flask was sealed and exposed to hydrogen gas under pressure and was stirred until the hydrogen consumption was completely stopped. The reaction mixture was filtered through celite. The solvent was evaporated to afford the desired product.

Step 3 (2-Hexyl-1-methyl-1H-indole)

To a solution of 2-hexyl-1H-indole in DMSO was added KOH at RT and was stirred for 30 minutes. Then to this mixture, iodomethane was added and stirred for 3 hours. The reaction mixture was treated with saturated ammonium chloride and ethyl acetate. The product was purified by column chromatography.

Step 4 (5-(2-Hexyl-1-methyl-1H-indol-3-yl)-5-oxo-pentanoic acid)

To a solution of 2-hexyl-1-methyl-1H-indole in methylene chloride at 0° C. was added dimethyl aluminum chloride solution in hexane. The reaction mixture was stirred for 30 minutes. To this solution dihydro-pyran-2,6-dione was added at 0° C. and the reaction mixture was stirred for 3 hours. The reaction was treated with saturated ammonium chloride and ethyl acetate. The product was purified by column chromatography.

Example 26

Compound #10 (5-(2-Hexyl-1H-indol-3-yl)-5-oxo-pentanoic acid) was prepared using the same procedure as described above for compound #5 but step 3 was not performed.

Example 27

Compound #60 (5-(5-Chloro-2-hexyl-1-methyl-1H-indol-3-yl)-3-methyl-5-oxo-pentanoic acid) was prepared using the same procedure as described above for compound #5 by using 5-chloro-1H-indole-2-carbaldehyde in step 1 and 4-methyl-dihydro-pyran-2,6-dione in step 4.

Example 28

Compound #61 ({1-[2-(2-Hexyl-1-methyl-1H-indol-3-yl)-2-oxo-ethyl]-cyclopropyl}-acetic acid) was prepared using the same procedure as described above for compound #5 by using 6-Oxa-spiro[2.5]octane-5,7-dione in step 4.

Example 29

Compound #22 (3,3-Dimethyl-5-oxo-5-(2-undecyl-indol-1-yl)-pentanoic acid) was prepared using the following procedure:

Step 1 (2-Undec-1-enyl-1H-indole)

To a suspension of decyl-triphenyl-phosphonium bromide in THF was added NaHMDS in THF and the mixture was stirred for 30 minutes and then the solution of 1H-indole-2-carbaldehyde was added to the reaction mixture and stirred for 3 hours. The reaction mixture was treated with saturated ammonium chloride and ethyl acetate. The product was purified by column chromatography.

Step 2 (2-undecyl-1H-indole)

2-undec-1-enyl-1H-indole was dissolved in ethanol and 10% palladium on carbon was added to the solution. The reaction flask was sealed and exposed to hydrogen gas under pressure and was stirred until hydrogen consumption was completely stopped. The reaction mixture was filtered through celite. The solvent was evaporated to afford the desired product.

Step 3 (3,3-Dimethyl-5-oxo-5-(2-undecyl-indol-1-yl)-pentanoic acid)

To a solution of 2-undecyl-1H-indole in DMSO was added KOH at RT and was stirred for 30 minutes. Then to this mixture 4,4-dimethyl-dihydro-pyran-2,6-dione was added and stirred for 3 hours. The reaction mixture was treated with saturated ammonium chloride and ethyl acetate. The product was purified by column chromatography.

Example 30

Compound #21 (5-(2-Hexyl-indol-1-yl)-3,3-dimethyl-5-oxo-pentanoic acid) was prepared similarly using the above procedure described for compound #22 by using pentyl-triphenyl-phosphonium bromide in step 1.

Example 31

Compound #58 (3-Methyl-5-(2-octyl-indol-1-yl)-5-oxo-pentanoic acid) was prepared using the following procedure:

Step 1 (2-Oct-1-enyl-1H-indole)

To a suspension of heptyl-triphenyl-phosphonium bromide in THF was added LiHMDS in THF and the mixture was stirred for 30 minutes and then the solution of 1H-indole-2-carbaldehyde was added to the reaction mixture and stirred for 3 hours. The reaction mixture was treated with saturated ammonium chloride and ethyl acetate. The product was purified by column chromatography.

Step 2 (2-Octyl-1H-indole)

2-Oct-1-enyl-1H-indole was dissolved in ethanol and 10% palladium on carbon was added to the solution. The reaction flask was sealed and exposed to hydrogen gas under pressure and was stirred until the hydrogen gas consumption was completely stopped. The reaction mixture was filtered through celite. The solvent was evaporated to afford the desired product.

Step 3 (3-Methyl-5-(2-octyl-indol-1-yl)-5-oxo-pentanoic acid)

To a solution of 2-octyl-1H-indole in DMSO was added KOH at RT and was stirred for 30 minutes. Then to this mixture 4-methyl-dihydro-pyran-2,6-dione was added and stirred for 3 hours. The reaction mixture was treated with saturated ammonium chloride and ethyl acetate. The product was purified by column chromatography.

Example 32

Compound #59 (5-(2-Butyl-indol-1-yl)-3-methyl-5-oxo-pentanoic acid) was prepared similarly using the above procedure described for compound #58 by using propyl-triphenyl-phosphonium bromide in step 1.

Example 33

Compound #34 (5-(2-Heptyl-indol-1-yl)-3-methyl-5-oxo-pentanoic acid) was prepared similarly by using the above procedure described for compound #58 by using hexyl-triphenyl-phosphonium bromide in step 1.

Example 34

Compound #57 (5-(5-Chloro-2-hexyl-indol-1-yl)-3-methyl-5-oxo-pentanoic acid) was prepared similarly using the above procedure described for compound #58 by using pentyl-triphenyl-phosphonium bromide and 5-chloro-1H-indole-2-carbaldehyde in step 1.

Example 35

Compound #102 (5-(1-Ethyl-2-hexyl-1H-indol-3-yl)-3-methyl-5-oxo-pentanoic acid) was prepared by the same procedure described for compound #5 (see Example 25) using iodoethane in step 3 and 4-Methyl-dihydro-pyran-2,6-dione in step 4.

Example 36

Compound #101 (5-(5-Chloro-1-ethyl-2-hexyl-1H-indol-3-yl)-3-methyl-5-oxo-pentanoic acid) was prepared by the same procedure described for compound #5 (see Example 25) using 5-Chloro-1H-indole-2-carbaldehyde in step 1, iodoethane in step 3 and 4-Methyl-dihydro-pyran-2,6-dione in step 4.

Example 37

Compound #104 (5-(6-Chloro-2-hexyl-1-methyl-1H-indol-3-yl)-3-methyl-5-oxo-pentanoic acid) was prepared by the same procedure described for compound #5 (see Example 25) using 6-Chloro-1H-indole-2-carbaldehyde in step 1 and 4-Methyl-dihydro-pyran-2,6-dione in step 4.

Example 38

Compound #109 (5-[6-Chloro-1-methyl-2-(5-methyl-hexyl)-1H-indol-3-yl]-3-methyl-5-oxo-pentanoic acid) was prepared by the same procedure described for compound #5 (see Example 25) using 6-Chloro-1H-indole-2-carbaldehyde and (4-Methyl-pentyl)-triphenyl-phosphonium bromide in step 1 and 4-Methyl-dihydro-pyran-2,6-dione in step 4.

Example 39

Compound #105 (5-(5-chloro-2-hexyl-1-methyl-1H-indol-3-yl)-3-methyl-5-oxo-N-(1-phenylethyl)pentanamide) was prepared by using steps 1 to 4 used for preparation of compound #5 (see Example 25) using 5-Chloro-1H-indole-2-carbaldehyde in step 1 and 4-Methyl-dihydro-pyran-2,6-dione in step 4.

Step 5: 5-(5-chloro-2-hexyl-1-methyl-1H-indol-3-yl)-3-methyl-5-oxo-N-(1-phenylethyl)pentanamide To the solution of 6-(5-chloro-2-hexyl-1-methyl-1H-indol-3-yl)-4-methyl-2,6-dioxohexanoic acid in methylene chloride was added (R)-1-phenylethanamine followed by the addition of DCC and DMAP and was stirred for 30 minutes. The reaction mixture was treated with sodium bicarbonate and methylene chloride. The product was purified by column chromatography.

Example 40

Compound #106 (5-(5-Chloro-2-hexyl-1-methyl-1H-indol-3-yl)-3-(R)-methyl-5-oxo-pentanoic acid (1-phenylethyl)-amide) was prepared by using steps 1 to 4 used for preparation of compound #5 (see Example 25) using 5-Chloro-1H-indole-2-carbaldehyde in step 1 and (S)-methyl 5-chloro-3-methyl-5-oxopentanoate in step 4 in place of anhydride.

Step 5: 5-(5-chloro-2-hexyl-1-methyl-1H-indol-3-yl)-3-(R)-methyl-5-oxopentanoic acid To the solution of Methyl-5-(5-chloro-2-hexyl-1-methyl-1H-indol-3-yl)-3-(R)-methyl-5-oxopentanoate in iso-propanol and water was added lithium hydroxide monohydrate and was stirred at RT for three hours. The product was purified by column chromatography.

Step 6: 5-(5-chloro-2-hexyl-1-methyl-1H-indol-3-yl)-3-(R)-methyl-5-oxo-N-(1-phenylethyl)pentanamide To the solution of 5-(5-chloro-2-hexyl-1-methyl-1H-indol-3-yl)-3-(R)-methyl-5-oxopentanoic acid in methylene chloride was added (R)-1-phenylethanamine followed by the addition of DCC and DMAP and was stirred for 30 minutes. The reaction mixture was treated with sodium bicarbonate and methylene chloride. The product was purified by column chromatography.

Example 41

Compound #108 (3-(5-Chloro-2-hexyl-1-methyl-1H-indole-3-carbonyl)benzoic acid) was prepared by using steps 1 to 4 used for preparation of compound #5 (see Example 25) using 5-Chloro-1H-indole-2-carbaldehyde in steps 1 and by using methyl 3-(chlorocarbonyl)benzoate in step 4 in place of anhydride.

Step 5: 3-(5-chloro-2-hexyl-1-methyl-1H-indole-3-carbonyl)benzoic acid

To the solution of methyl 3-(5-chloro-2-hexyl-1-methyl-1H-indole-3-carbonyl) benzoate in iso-propanol and water was added lithium hydroxide monohydrate and was stirred at RT for three hours. The product was purified by column chromatography.

Example 42

Compound #100 was prepared using the following procedure:

Step 1: 5-Chloro-2-hex-1-enyl-1H-indole

To the cold suspension of Pentyl-triphenyl-phosphonium bromide in THF was added LiHMDS in THF and the mixture was stirred for 30 minutes. A solution of 5-Chloro-1H-indole-2-carbaldehyde in THF was added to the reaction mixture and stirred for 3 hours. The reaction mixture was treated with saturated ammonium chloride and ethyl acetate. The product was purified by column chromatography.

Step 2: 5-Chloro-2-hexyl-1H-indole

5-Chloro-2-hex-1-enyl-1H-indole was dissolved in ethanol and 10% palladium on carbon was added to the solution. The reaction flask was sealed and exposed to hydrogen gas under pressure and was stirred for 5 hours. Then the reaction mixture was filtered through Celite. The solvent was evaporated to give 5-Chloro-2-hexyl-1H-indole

Step 3: 5-Chloro-2-hexyl-1-methyl-1H-indole

To the solution 5-Chloro-2-hexyl-1H-indole in DMSO was added KOH at RT and was stirred for 30 minutes. Then to this mixture, iodomethane was added and stirred for 3 hours. The reaction was quenched with saturated ammonium chloride solution and extracted with ethyl acetate. The product, 5-Chloro-2-hexyl-1-methyl-1H-indole was purified by column chromatography.

Step 4: Methyl-5-(5-chloro-2-hexyl-1-methyl-1H-indol-3-yl)-3-(R)-methyl-5-oxopentanoate To the cold solution of 5-Chloro-2-hexyl-1-methyl-1H-indole in methylene chloride was added dimethyl aluminum chloride solution and was stirred for 30 minutes. Then (S)-methyl 5-chloro-3-methyl-5-oxopentanoate in methylene chloride was added to the reaction mixture and was stirred for 3 hours. The reaction mixture was then treated with saturated ammonium chloride and ethyl acetate. The product was purified by column chromatography.

Step 5: 5-(5-chloro-2-hexyl-1-methyl-1H-indol-3-yl)-3-(R)-methyl-5-oxopentanoic acid To the solution of Methyl 5-(5-chloro-2-hexyl-1-methyl-1H-indol-3-yl)-3-(R)-methyl-5-oxopentanoate in iso-propanol and water was added lithium hydroxide monohydrate and was stirred at RT for three hours. The product was purified by column chromatography.
Ref#1

Preparation of 4-Chlorocarbonyl-3-(R)-methyl-butyric acid 2-trimethylsilanyl-ethyl ester

Step 1: 3-(S)-Methyl-pentanedioic acid methyl ester 2-trimethylsilanyl-ethyl ester To the solution of 3-(R)-Methyl-pentanedioic acid monomethyl ester in methylene chloride was added 2-Trimethylsilanyl-ethanol followed by DCC and DMAP and was stirred for 30 minutes. The reaction mixture was treated with sodium bicarbonate and methylene chloride. The product was purified by column chromatography.

Step 2: 3-(S)-Methyl-pentanedioic acid mono-(2-trimethylsilanyl-ethyl) ester

To the solution of 3-(S)-Methyl-pentanedioic acid methyl ester 2-trimethylsilanyl-ethyl ester in iso-propanol and water was added lithium hydroxide monohydrate and stirred for two hours at RT. The reaction mixture was treated with saturated ammonium chloride and ethyl acetate. The product was purified by column chromatography.

Step 3: R-4-Chlorocarbonyl-3-methyl-butyric acid 2-trimethylsilanyl-ethyl ester

To the cold solution of 3-(S)-Methyl-pentanedioic acid mono-(2-trimethylsilanyl-ethyl) ester in methylene chloride was added oxalyl chloride followed by DMF and was stirred for two hours. The solvent was evaporated and the product was dried under vacuum.

Example 43

Compound #107 was prepared using the following procedure:

Step 1: 5-Chloro-2-hex-1-enyl-1H-indole

To the cold suspension of pentyl triphenyl-phosphonium bromide in THF was added LiHMDS in THF and the mixture was stirred for 30 minutes and then the solution of 5-chloro-1H-indole-2-carbaldehyde was added to the reaction mixture and stirred for 3 hours. The reaction was quenched with saturated ammonium chloride solution and extracted with ethyl acetate. The product, 5-chloro-2-hex-1-enyl-1H-indole was purified by column chromatography.

Step 2: 5-Chloro-2-hexyl-1H-indole

5-Chloro-2-hex-1-enyl-1H-indole was dissolved in ethanol and 10% palladium on carbon was added to the solution. The reaction flask was sealed and exposed to hydrogen gas under pressure and was stirred for 5 hours. Then the reaction mixture was filtered through Celite. The solvent was evaporated to give 5-chloro-2-hexyl-1H-indole.

Step 3: 5-Chloro-2-hexyl-1-methyl-1H-indole

To the solution of 5-chloro-2-hexyl-1H-indole in DMSO was added KOH at RT and was stirred for 30 minutes. Then to this mixture, iodomethane was added and stirred for 3 hours. The reaction was quenched with saturated ammonium chloride solution and extracted with ethyl acetate. The product, 5-chloro-2-hexyl-1-methyl-1H-indole was purified by column chromatography.

Step 4: 5-(6-Chloro-2-hexyl-indol-1-yl)-3-(S)-methyl-5-oxo-pentanoic acid (tert-butyl-diphenyl-silanyl)-methyl ester To the solution of 5-chloro-2-hexyl-1-methyl-1H-indole in methylene chloride was added dimethyl aluminum chloride at 0 0 C and was stirred for 60 minutes. Then to this mixture, 4-chlorocarbonyl-3-(R)-methyl-butyric acid (tert-butyl-diphenyl-silanyl)-methyl ester was added and stirred for 3 hours. The reaction was quenched with saturated ammonium chloride solution and extracted with ethyl acetate. The product was purified by column chromatography.

Step 5: 5-(5-Chloro-2-hexyl-1-methyl-1H-indol-3-yl)-3-(R)-methyl-5-oxo-pentanoic acid To the solution of 5-(6-Chloro-2-hexyl-indol-1-yl)-3-(S)-methyl-5-oxo-pentanoic acid (tent-butyl-diphenyl-silanyl)-methyl ester in isopropanol:water was added lithium hydroxide and was stirred for 1 day. The reaction was quenched with saturated ammonium chloride solution and extracted with ethyl acetate. The product was purified by column chromatography.

Example 44

Compound #103 (5-(6-Chloro-2-hexyl-indol-1-yl)-3-methyl-5-oxo-pentanoic acid) was prepared by the same procedure described for compound #2 (see Example 8) by using 6-Chloro-1H-indole-2-carbaldehyde in step 1.

Example 45

Compound #110 (5-[6-Chloro-2-(5-methyl-hexyl)-indol-1-yl]-3-methyl-5-oxo-pentanoic acid) was prepared by the same procedure described for compound #2 (see Example 8) by using 6-Chloro-1H-indole-2-carbaldehyde and (4-Methyl-pentyl)-triphenyl-phosphonium bromide in step 1.

Example 46

Compound #111 was prepared using the following procedure:

Step 1: 6-Chloro-2-hex-1-enyl-1H-indole

To the cold suspension of Pentyl-triphenyl-phosphonium bromide in THF was added LiHMDS in THF and the mixture was stirred for 30 minutes. A solution of 6-Chloro-1H-indole-2-carbaldehyde in THF was added to the reaction mixture and stirred for 3 hours. The reaction mixture was treated with saturated ammonium chloride and ethyl acetate. The product was purified by column chromatography.

Step 2: 6-Chloro-2-hexyl-1H-indole

6-Chloro-2-hex-1-enyl-1H-indole was dissolved in ethanol and 10% palladium on carbon was added to the solution. The reaction flask was sealed and exposed to hydrogen gas under pressure and was stirred for 5 hours. Then the reaction mixture was filtered through Celite. The solvent was evaporated to give 6-Chloro-2-hexyl-1H-indole.

Step 3: 5-(6-Chloro-2-hexyl-indol-1-yl)-3-(S)-methyl-5-oxo-pentanoic acid 2-trimethylsilanyl-ethyl ester To the cold solution of 6-Chloro-2-hexyl-1H-indole in methylene chloride was added a solution of potassium tert-butoxide in THF and stirred for 30 minutes. Then R-4-Chlorocarbonyl-3-methyl-butyric acid 2-trimethylsilanyl-ethyl ester (Ref #1: Preparation as described above) in methylene chloride was added to the reaction mixture and was stirred for 3 hours. The reaction mixture was then treated with saturated ammonium chloride and ethyl acetate. The product was purified by column chromatography.

Step 4: 5-(6-Chloro-2-hexyl-indol-1-yl)-3-(S)-methyl-5-oxo-pentanoic acid

To the cold solution of 5-(6-Chloro-2-hexyl-indol-1-yl)-3-(S)-methyl-5-oxo-pentanoic acid 2-trimethylsilanyl-ethyl ester in methylene chloride was added trifluoro acetic acid and was stirred for three days. The reaction mixture was then treated with water and ethyl acetate. The product was purified by column chromatography.

Example 47

Compound #112 was prepared using the following procedure:

Step 1: 6-Chloro-2-hex-1-enyl-1H-indole

To the cold suspension of Pentyl-triphenyl-phosphonium bromide in THF was added LiHMDS in THF and the mixture was stirred for 30 minutes. A solution of 6-Chloro-1H-indole-2-carbaldehyde in THF was added to the reaction mixture and stirred for 3 hours. The reaction mixture was treated with saturated ammonium chloride and ethyl acetate. The product was purified by column chromatography.

Step 2: 6-Chloro-2-hexyl-1H-indole

6-Chloro-2-hex-1-enyl-1H-indole was dissolved in ethanol and 10% palladium on carbon was added to the solution. The reaction flask was sealed and exposed to hydrogen gas under pressure and was stirred for 5 hours. Then the reaction mixture was filtered through Celite. The solvent was evaporated to give 6-Chloro-2-hexyl-1H-indole.

Step 3: 5-(6-Chloro-2-hexyl-indol-1-yl)-3(R)-methyl-5-oxo-pentanoic acid methyl ester To the cold solution of 6-Chloro-2-hexyl-1H-indole in methylene chloride was added solution of potassium tert-butoxide in THF and stirred for 30 minutes. Then (S)-methyl 5-chloro-3-methyl-5-oxopentanoate in methylene chloride was added to the reaction mixture and was stirred for 3 hours. The reaction mixture was then treated with saturated ammonium chloride and ethyl acetate. The product was purified by column chromatography.

Step 4: 5-(6-Chloro-2-hexyl-indol-1-yl)-3-(R)-methyl-5-oxo-pentanoic acid

To the solution of 5-(6-Chloro-2-hexyl-indol-1-yl)-3-(R)-methyl-5-oxo-pentanoic acid methyl ester in THF was added 1.2N HCL and was stirred at 60 0 C for 30 hours. The reaction mixture was then treated with water and ethyl acetate. The product was purified by column chromatography.

Example 48

Compound #36, (5-(5-Chloro-2-hexyl-indol-1-yl)-3-(S)-methyl-5-oxo-pentanoic acid), described above and in US Provisional Patent Application #61/175,175, was prepared by the same procedure as described for compound 111 using 5-Chloro-1H-indole-2-carbaldehyde in step1.

Example 49

Compound #113 was prepared using the following procedure:

Step 1: 5-Chloro-2-hept-1-enyl-1H-indole

To the cold suspension of hexyl-triphenyl-phosphonium bromide in THF was added LiHMDS in THF and the mixture was stirred for 30 minutes and then the solution of 5-chloro-1H-indole-2-carbaldehyde was added to the reaction mixture and stirred for 3 hours. The reaction was quenched with saturated ammonium chloride solution and extracted with ethyl acetate. The product, 5-chloro-2-hept-1-enyl-1H-indole was purified by column chromatography.

Step 2: 5-Chloro-2-heptyl-1H-indole

5-Chloro-2-hept-1-enyl-1H-indole was dissolved in ethanol and 10% palladium on carbon was added to the solution. The reaction flask was sealed and exposed to hydrogen gas under pressure and was stirred for 5 hours. Then the reaction mixture was filtered through Celite. The solvent was evaporated to give 5-chloro-2-heptyl-1H-indole.

Step 3: 5-Chloro-2-heptyl-1-methyl-1H-indole

To the solution of 5-chloro-2-heptyl-1H-indole in DMSO was added KOH at RT and was stirred for 30 minutes. Then to this mixture, iodomethane was added and stirred for 3 hours. The reaction was quenched with saturated ammonium chloride solution and extracted with ethyl acetate. The product, 5-chloro-2-heptyl-1-methyl-1H-indole was purified by column chromatography.

Step 4: 5-(5-Chloro-2-heptyl-1-methyl-1H-indol-3-yl)-3-methyl-5-oxo-pentanoic acid To the solution of 5-chloro-2-heptyl-1-methyl-1H-indole in methylene chloride at 0° C. was added dimethyl aluminum chloride solution in hexane. The reaction mixture was stirred for 30 minutes. To this solution 4-methyl-dihydro-pyran-2,6-dione was added at 0° C. and the reaction mixture was stirred for 3 hours. The reaction was quenched with saturated ammonium chloride solution and extracted with ethyl acetate. The product was purified by column chromatography.

Example 50

Compound #114 (5-[5-Chloro-1-methyl-2-(5-methyl-hexyl)-1H-indol-3-yl]-3-methyl-5-oxo-pentanoic acid) was prepared by the same procedure described for compound #113. But (4-methyl-pentyl)-triphenyl-phosphonium bromide was used in step 1.

Example 51

☐Compound #115 was prepared using the following procedure:

Step 1: 5-Chloro-2-(5-methyl-hex-1-enyl)-1H-indole

To the cold suspension of (4-methyl-pentyl)-triphenyl-phosphonium bromide in THF was added LiHMDS in THF and the mixture was stirred for 30 minutes and then the solution of 5-chloro-1H-indole-2-carbaldehyde was added to the reaction mixture and stirred for 3 hours. The reaction was quenched with saturated ammonium chloride solution and extracted with ethyl acetate. The product, 5-chloro-2-(5-methyl-hex-1-enyl)-1H-indole was purified by column chromatography.

Step 2: 5-Chloro-2-(5-methyl-hexyl)-1H-indole

5-Chloro-2-(5-methyl-hex-1-enyl)-1H-indole was dissolved in ethanol and 10% palladium on carbon was added to the solution. The reaction flask was sealed and exposed to hydrogen gas under pressure and was stirred for 5 hours. Then the reaction mixture was filtered through Celite. The solvent was evaporated to give 5-chloro-2-(5-methyl-hexyl)-1H-indole.

Step 3: 5-[5-Chloro-2-(5-methyl-hexyl)-indol-1-yl]-3-methyl-5-oxo-pentanoic acid To the solution of 5-chloro-2-(5-methyl-hexyl)-1H-indole in DMSO was added KOH at RT and was stirred for 30 minutes. Then to this mixture, 4-methyl-dihydro-pyran-2,6-dione was added and stirred for 3 hours. The reaction was quenched with saturated ammonium chloride solution and extracted with ethyl acetate. The product was purified by column chromatography.

Example 52

Compound #116 (5-(6-Chloro-2-hexyl-indol-1-yl)-2,2-dimethyl-5-oxo-pentanoic acid) was prepared by the same procedure described for compound #115 but by using pentyl-triphenyl-phosphonium bromide and 6-Chloro-1H-indole-2-carbaldehyde step1 and 3,3-Dimethyl-dihydro-pyran-2,6-dione was used in step 3.

Example 53

☐Compound #117 was prepared using the following procedure:

Step1: 2-Hexyl-quinolin-3-ylamine

To the solution of quinolin-3-ylamine in ether was added tert-butyl lithium at −78° C. and was stirred for 2 hours. To the reaction mixture was added the solution of 1-Iodo-hexane in ether and was allowed to warm up to RT. The reaction was continued for 1 day. The reaction was quenched with saturated ammonium chloride solution and extracted with chloroform. The product was purified by column chromatography.

Step2: 3-Bromo-2-hexyl-quinoline

To the solution of 2-hexyl-quinolin-3-ylamine in hydrobromic acid at -10° C. was added aqueous solution of sodium nitrite followed by bromine and was allowed to warm up to RT. The reaction was continued for 1 day. Next day the reaction mixture was neutralized using aqueous ammonium hydroxide solution and was extracted with ether. The organic layer was washed with aqueous sodium thiosulfate. The product was purified by column chromatography.

Step3: 5-(2-Hexyl-quinolin-3-yl)-5-oxo-pentanoic acid

To the solution of 3-bromo-2-hexyl-quinoline in ether was added tert-butyl lithium at −100° C. The reaction mixture was stirred for 2 hours at −100° C. To the reaction mixture a solution of dihydro-pyran-2,6-dione in ether was added at −100° C. and stirred for 30 minutes and was allowed to warm up to RT. The stirring was continued for 3 hours. The water was added to the reaction mixture and was stirred for 20 minutes. Solvent was evaporated under vacuum and water was added to the crude mixture. It was then acidified by using dilute HCl and was extracted with ether. The product was purified by column chromatography.

Example 54

Compound #118 (5-(2-Hexyl-quinolin-3-yl)-3-methyl-5-oxo-pentanoic acid) was prepared by the same procedure described for compound #117 but 4-methyl-dihydro-pyran-2,6-dione was used in step 3.

Biological Assays

Compounds of the invention can be tested to determine their activity as antagonists of the OXE receptor and/or blockers of biological responses to 5-oxo-ETE using a variety of assays which are known in the art. For example, assays for inhibition of 5-oxo-ETE-induced calcium mobilization, actin polymerization and chemotaxis in neutrophils are used to determine 5-oxo-ETE antagonist properties of representative compounds of the present invention. In addition the levels of representative compounds of the invention in blood are measured by HPLC following oral administration to rats.

Primary Screening for Antagonist Activity: Calcium Mobilization in Human Granulocytes Human granulocytes (≥95% neutrophils) are prepared from whole blood using Dextran 500 to remove red blood cells, followed by centrifugation over Ficoll-Paque to remove mononuclear cells and hypotonic lysis of any remaining red blood cells. After centrifugation the granulocytes are suspended in $Ca^{++}/Mg^{++}$-free phosphate-buffered saline (PBS$^-$). Granulocytes ($10^7$ cells/nil) are incubated with the acetoxymethyl ester of indo-1 (1 μM) for 30 min, followed by washing twice with PBS$^-$ and resuspension in the same medium to obtain a final cell concentration of $3.22 \times 10^6$ cells/ml. Five minutes prior to commencing data acquisition, $Ca^{++}$ and $Mg^{++}$ are added to give final concentrations of 1.8 and 1 mM, respectively. Calcium measurements are performed at 37° C. using a spectrofluorometer equipped with a temperature-controlled cuvette holder and a magnetic stirrer. The excitation and emission wavelengths are 331 nm and 410 nm, respectively. Following stabilization of the baseline, fluorescence is measured for 1 min, prior to the addition of either vehicle or various concentrations of a potential 5-oxo-ETE antagonist. Two min later, 5-oxo-ETE (10 nM) is added, followed 1 min later by digitonin (final concentration 0.1%). Data acquisition is terminated after a further 0.5 min. In some cases $LTB_4$ (10 nM) is added 2 min after 5-oxo-ETE, followed 0.5 min later by addition of digitonin. $F_{max}$ is determined from fluorescence measurements after the addition of digitonin, whereas $F_{min}$ is determined after determination of autofluorescence as described in the literature (Gelfand et al, J. Biol. Chem. 261: 11520 (1986)). A dissociation constant of 250 nM for the indo-1/$Ca^{++}$ complex is used to calculate $[Ca^{++}]_i$. The % inhibition of 5-oxo-ETE-induced calcium mobilization by the antagonist is calculated as follows:

$$\text{Inhibition}(\%) = (1 - (Ca_{ant}/Ca^{++}_{veh})) \times 100$$

where $Ca_{ant}$ is the increase in cytosolic calcium levels induced by 5-oxo-ETE (10 nM) following the addition of a potential antagonist, whereas $Ca_{veh}$ is the response induced by 5-oxo-ETE following addition of vehicle alone.

Measurement of Actin Polymerization in Eosinophils

F-actin levels in eosinophils are measured using unfractionated leukocytes, prepared as described above. Leukocytes ($5\times10^7$ cells/mil) are treated with PC5-labeled mouse anti-human CD16 (10 µl/$10^6$ cells; Beckman-Coulter) for 30 min on ice. PBS (2 ml/$10^6$ cells) is then added and the mixture centrifuged at 200×g for 10 min. The pellet is resuspended in ice cold PBS containing $Ca^{++}$ (1.8 mM) and $Mg^{++}$ (1 mM) to give a concentration of $5\times10^6$ cells/ml. Aliquots (90 µl) of the leukocyte suspension are first incubated at 37° C. with either vehicle (10 µl PBS containing $Ca^{++}$ and $Mg^{++}$ and 0.1% BSA) or vehicle containing a 5-oxo-ETE antagonist. After 5 min, either vehicle or vehicle containing 5-oxo-ETE (final concentration, 10 nM) is added and the incubation continued for a further 20 s. The incubations are then terminated by addition of formaldehyde (37%) to give a final concentration of 8.5%. After keeping the samples on ice for 30 min, a mixture of lysophosphatidylcholine (30 µg in 23.8 µl PBS) and N-(7-nitrobenz-2-oxa-1,3-diazol-4-yl)phallacidin (NBD-phallacidin); Molecular Probes; 49 pmol in 6.2 µl methanol; final concentration, 0.3 µM) is added to each sample, followed by incubation overnight in the dark at 4° C. The cells are then washed by addition of PBS (1 ml), followed by centrifugation at 200×g for 10 min and resuspension of the pellet in 300 µl PBS containing 1% formaldehyde. F-actin levels are measured by flow cytometry in eosinophils, which are gated based on high side scatter and low staining with anti-CD16. F-actin levels in the eosinophil population are assessed on the basis of fluorescence due to staining with NBD-phallacidin.

Neutrophil Migration

Cell migration is measured by the modified Boyden technique using 48-well microchemotaxis chambers and Sartorius cellulose nitrate filters (8 µm pore size; 140 µm thickness) as described previously (Powell et al., J Immunol 156: 336 (1996)). Granulocytes (≥95% neutrophils) are prepared as described above. Immediately prior to use the filters are soaked in PBS containing calcium (1 mM), magnesium (1 mM), and 0.3% BSA. Either vehicle (PBS containing $Ca^{++}$, $Mg^{++}$, and 0.3% BSA) or vehicle containing 5-oxo-ETE (100 nM final concentration) is added to the bottom well in a volume of 30 µl, whereas neutrophils (150,000 cells in 55 µl PBS containing $Ca^{++}$, $Mg^{++}$ and 0.4% ovalbumin) and either vehicle or various concentrations of a 5-oxo-ETE antagonist are added to each of the top wells. The chambers are incubated for 2 h at 37° C. in 5% $CO_2$ and humidified air. The filters are then fixed by overnight immersion in a saturated solution of mercuric chloride in 50% aqueous ethanol and the cells are stained using hematoxylin followed by chromotrope 2R. The filters are mounted on slides with coverslips using Permount and the numbers of cells on the bottom surfaces of the filters are counted in 5 different fields at a magnification of 400× for each incubation, each of which is performed in triplicate. In cases in which there are large numbers of cells on the bottom surfaces of the filters only quarter or half fields are counted and the results corrected accordingly.

Measurement of Antagonist Concentrations in Blood Following Oral Administration

Antagonists dissolved in ethanol (100 µl) were added to 1 ml 20 mM $NaHCO_3$ pH 8.0. The resulting suspension was administered by gavage (1.1 ml containing a dose of between 5 and 30 mg/kg) to Sprague-Dawley rats (200-250 g). The rats were fasted for 3 h prior to the gavage. After different times (between 20 min and 6 h) the animals were euthanized with $CO_2$ and blood was withdrawn by cardiac puncture. To measure the concentrations of compounds 60 and 103 in blood, compounds 109 and 116, respectively, were used as internal standards. The appropriate internal standard (2 µg of 109 or 1 µg of 116), was immediately added to the blood sample after collection. The blood was centrifuged to remove blood cells and the plasma was added to MeOH (2 volumes) and stored overnight at −80° C. After removal of the sample from the freezer the protein precipitate was removed by centrifugation and the analytes were extracted on C18 SepPak cartridges (Waters Corp; Powell, Prostaglandins 20:947 (1980)). The amounts of the above compounds were determined by reversed-phase HPLC using UV detection. Antagonist concentration was determined by comparing the peak area for the antagonist in question with that for the corresponding internal standard and correcting for any difference in extinction coefficient.

Example 55

A series of compounds was tested for OXE receptor antagonist activity by assaying the compounds using the methods described above. Results are shown in Tables 2 to 7 below, which indicate the $IC_{50}$ values for the effects of 5-oxo-ETE receptor antagonists on 5-oxo-ETE-induced calcium mobilization ($Ca^{++}$) and chemotaxis in human granulocytes and actin polymerization (i.e. F-actin levels) in human eosinophils. All values are in µM. Compound numbers refer to Table 1.

TABLE 2

| Antagonist | $IC_{50}$ (µM) | | |
|---|---|---|---|
| | $Ca^{++}$ | Chemotaxis | F-Actin |
| 5-(2-Hexyl-1-methyl-1H-indol-3-yl)-5-oxo-pentanoic acid (compound no. 5) | 2.5 | | |
| 5-(2-Hexyl-indol-1-yl)-5-oxo-pentanoic acid (compound no. 1) | 1 | | |
| 5-(2-Hexyl-1-methyl-1H-indol-3-yl)-3-methyl-5-oxo-pentanoic acid (compound no. 6) | 0.34 | | |
| 5-(2-Hexyl-indol-1-yl)-3-methyl-5-oxo-pentanoic acid (compound no. 2) | 0.09 | 0.82 | 0.46 |
| 5-(5-Chloro-2-hexyl-1-methyl-1H-indol-3-yl)-1-methyl-5-oxo-pentanoic acid (compound no. 60) | 0.025 | 0.11 | 0.072 |
| Compound no. 100 | 0.125 | | |
| Compound no. 101 | 0.350 | | |
| Compound no. 102 | 1.6 | | |
| Compound no. 103 | 0.025 | | |
| Compound no. 104 | 0.119 | | |
| Compound no. 105 | >10 | | |
| Compound no. 106 | >10 | | |
| Compound no. 107 | 0.009 | | |
| Compound no. 108 | 0.065 | | |
| Compound no. 109 | 0.175 | | |
| Compound no. 110 | 1.030 | | |
| Compound no. 111 | 0.016 | | |
| Compound no. 112 | 0.460 | | |
| Compound no. 113 | 0.035 | | |
| Compound no. 114 | 0.011 | | |
| Compound no. 115 | 2.0 | | |
| Compound no. 116 | >10 | | |

TABLE 3

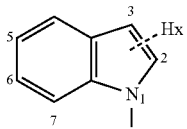

| | Cpd # | IC$_{50}$ (μM) |
|---|---|---|
| 2-Hexyl | 1 | 1.0 |
| 3-Hexyl | 7 | >30 |
| 5-Hexyl | 30 | >30 |
| 5-(1-Hexenyl) | 28 | 6.5 |
| 6-Hexyl | 31 | >10 |
| 7-Hexyl | 27 | >30 |
| 7-(1-Hexenyl) | 32 | >10 |

TABLE 4

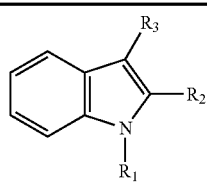

| R$_1$ | R$_2$ | R$_3$ | Cpd # | IC$_{50}$ (μM) |
|---|---|---|---|---|
| Hx | H | oV | 8 | >30 |
| H | Hx | oV | 10 | 11 |
| Me | Hx | oV | 5 | 3.7 |
| Me | oV | Hx | 11 | >30 |

TABLE 5

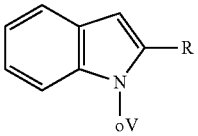

| | Cpd # | IC$_{50}$ (μM) |
|---|---|---|
| Butyl | 26 | >30 |
| Pentyl | 18 | 1.1 |
| Hexyl | 1 | 1.0 |
| Hexyl-5-Cl | 29 | 1.4 |
| 1-Hexenyl | 12 | 3.3 |
| Heptyl | 33 | 1.5 |
| Octyl | 25 | 2.7 |
| Undecyl | 23 | 25 |
| 1-Undecenyl | 20 | 20 |

TABLE 6

| | Cpd # | IC$_{50}$ (μM) |
|---|---|---|
|  | 16 | 4.5 |
|  | 14 | >10 |

TABLE 6-continued

| | Cpd # | IC$_{50}$ (μM) |
|---|---|---|
|  | 1 | 1.0 |
| (3Me-oV) | 2 | 0.09 |
| (3(R)-Me-oV) | 3 | 0.8 |
|  | 21 | 13 |

TABLE 7

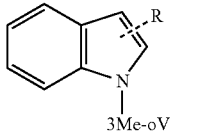

| | Cpd # | IC$_{50}$ (μM) |
|---|---|---|
| 2-Pentyl | 19 | 0.10 |
| 2-Hexyl | 2 | 0.09 |
| 2-Heptyl | 34 | 0.12 |
| 5-(1-hexenyl) | 17 | 10 |

The contents of all documents and references cited herein are hereby incorporated by reference in their entirety.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound of Formula II:

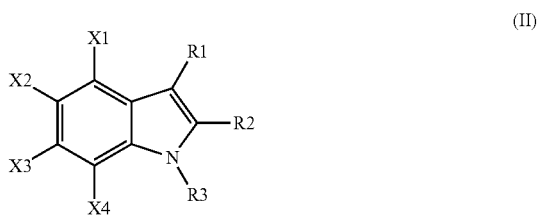

wherein:
X$_1$, X$_2$, X$_3$ and X$_4$ are independently selected from the group consisting of H, halogen, alkyl group, aralkyl group and OR$_5$ wherein R$_5$ is selected from the group consisting of H, acyl, alkyl, aralkyl, alkenyl, alkoxy, aryl, haloalkyl, cycloalkyl, haloalkoxy, heterocycloalkyl, cycloalkenyl and heterocycloalkenyl, any of which may be optionally substituted; and i) $R_3$ is selected from H and an alkyl group having 4 or more carbon atoms, one of $R_1$ or $R_2$ is an alkyl group having 4 or more carbon atoms and optionally substituted with $C_{6-16}$ aryl, or $C_{3-7}$ cycloalkyl, and the other of said $R_1$ or $R_2$ is

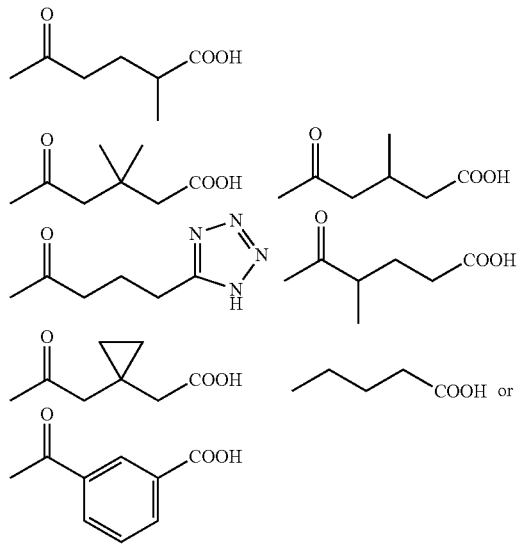

or ii) $R_3$ is

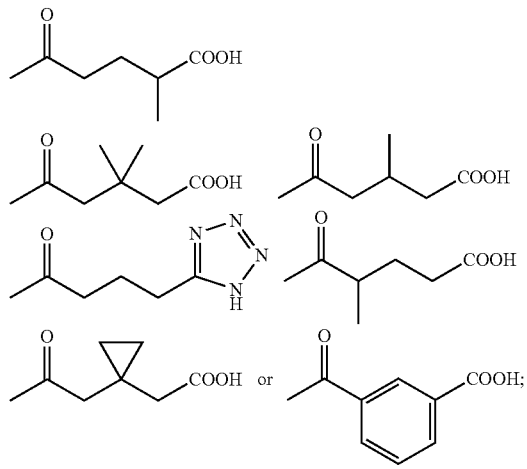

and $R_1$ is selected from H and an alkyl group having 4 or more carbon atoms, and $R_2$ is an alkyl group having 4 or more carbon atoms and optionally substituted with $C_{6-16}$ aryl, or $C_{3-7}$ cycloalkyl; or iii) $R_1$, $R_2$ and $R_3$ are each selected from H and an alkyl group having 4 or more carbon atoms, wherein at least one of $R_1$, $R_2$ and $R_3$ is an alkyl group having 4 or more carbon atoms, and at least one of $R_1$, $R_2$ and $R_3$ is

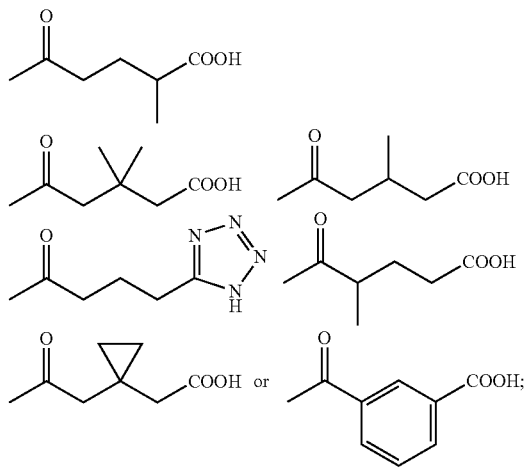

or a pharmaceutically acceptable salt thereof.

2. A pharmaceutical composition comprising a therapeutically effective amount of a compound of Formula II:

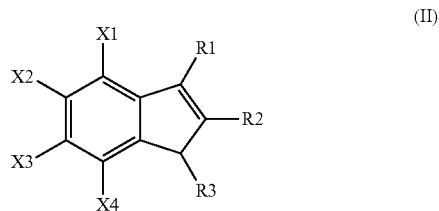

(II)

wherein:

$X_1$, $X_2$, $X_3$ and $X_4$ are independently selected from the group consisting of H, halogen, alkyl group, aralkyl group and $OR_5$ wherein $R_5$ is selected from the group consisting of H, acyl, alkyl, aralkyl, alkenyl, alkoxy, aryl, haloalkyl, cycloalkyl, haloalkoxy, heterocycloalkyl, cycloalkenyl and heterocycloalkenyl, any of which may be optionally substituted; and i) $R_3$ is selected from H and an alkyl group having 4 or more carbon atoms, one of $R_1$ or $R_2$ is an alkyl group having 4 or more carbon atoms and optionally substituted with $C_{6-16}$ aryl, or $C_{3-7}$ cycloalkyl, and the other of said $R_1$ or $R_2$ is

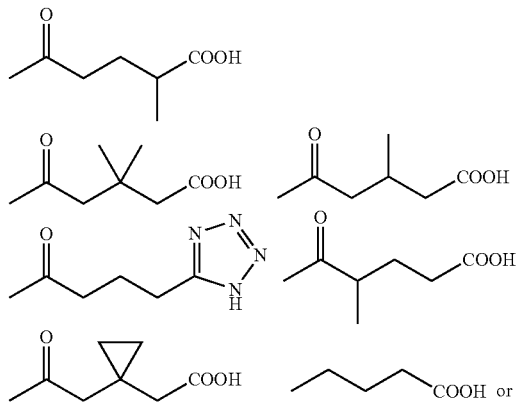

-continued

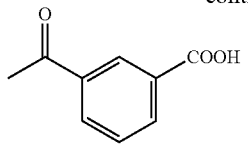

or ii) $R_3$ is

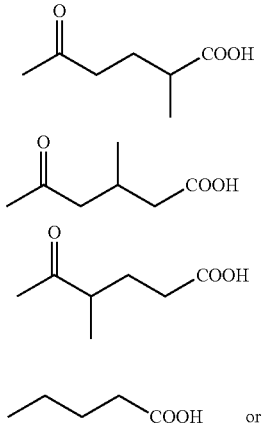 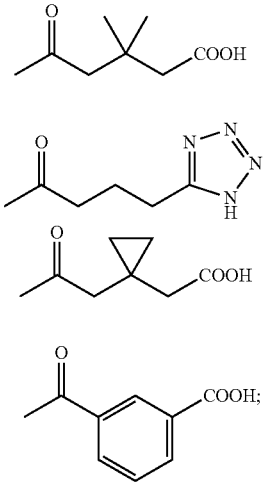

and $R_1$ is selected from H and an alkyl group having 4 or more carbon atoms, and $R_2$ is an alkyl group having 4 or more carbon atoms and optionally substituted with $C_{6-16}$ aryl, or $C_{3-7}$ cycloalkyl; or iii) $R_1$, $R_2$ and $R_3$ are each selected from H and an alkyl group having 4 or more carbon atoms, wherein at least one of $R_1$, $R_2$ and $R_3$ is an alkyl group having 4 or more carbon atoms, and at least one of $R_1$, $R_2$ and $R_3$ is

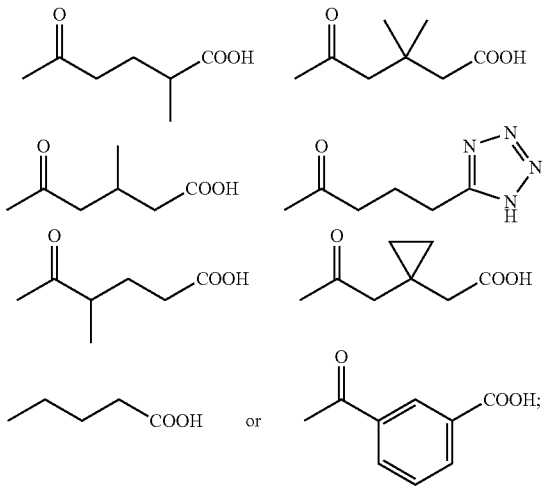

or a pharmaceutically acceptable salt thereof;
and a pharmaceutically acceptable carrier.

3. A method of treating a respiratory condition in a subject comprising administering to the subject a therapeutically effective amount of a compound of Formula II:

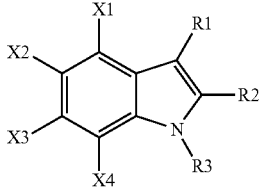

(II)

wherein:

$X_1$, $X_2$, $X_3$ and $X_4$ are independently selected from the group consisting of H, halogen, alkyl group, aralkyl group and $OR_5$ wherein $R_5$ is selected from the group consisting of H, acyl, alkyl, aralkyl, alkenyl, alkoxy, aryl, haloalkyl, cycloalkyl, haloalkoxy, heterocycloalkyl, cycloalkenyl and heterocycloalkenyl, any of which may be optionally substituted; and i) $R_3$ is selected from H and an alkyl group having 4 or more carbon atoms, one of $R_1$ or $R_2$ is an alkyl group having 4 or more carbon atoms and optionally substituted with $C_{6-16}$ aryl, or $C_{3-7}$ cycloalkyl, and the other of said $R_1$ or $R_2$ is

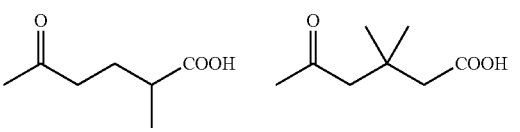
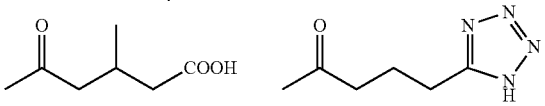
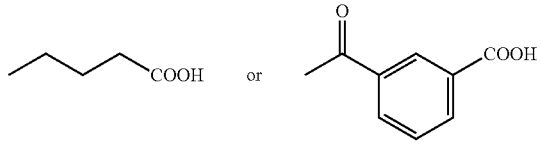
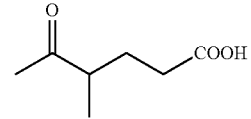

or ii) $R_3$ is

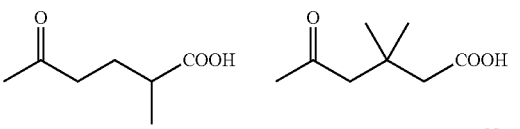
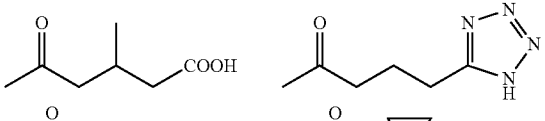
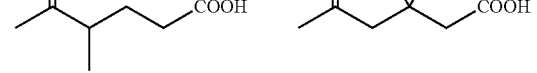

-continued

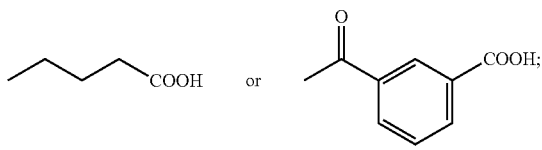

and

R₁ is selected from H and an alkyl group having 4 or more carbon atoms, and R₂ is an alkyl group having 4 or more carbon atoms and optionally substituted with $C_{6-16}$ aryl, or $C_{3-7}$ cycloalkyl; or iii) R₁, R₂ and R₃ are each selected from H and an alkyl group having 4 or more carbon atoms, wherein at least one of R₁, R₂ and R₃ is an alkyl group having 4 or more carbon atoms, and at least one of R₁, R₂ and R₃ is

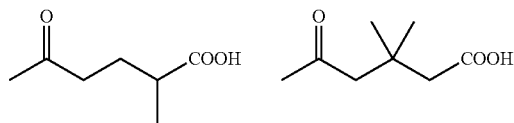

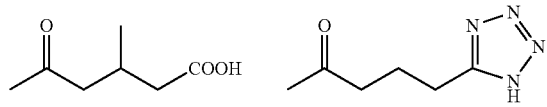

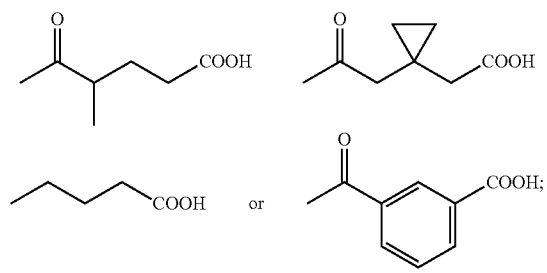

or a pharmaceutically acceptable salt thereof;
wherein the respiratory condition is asthma, allergic rhinitis, chronic obstructive pulmonary disease or idiopathic pulmonary fibrosis.

4. The method of claim 3, wherein the respiratory condition is associated with inflammation.

5. The method of claim 3, wherein the subject is a human.

6. The method of claim 3, further comprising concomitant administration of a second agent to the subject, wherein the second agent is an analgesic, anti-inflammatory agent or anti-allergy agent.

7. The method of claim 6, wherein the compound and the second agent are administered at the same time.

8. The method of claim 6, wherein the compound and the second agent are administered sequentially.

9. The method of claim 6, wherein the second agent is an NSAID, a bronchodilator or a leukotriene modifier.

10. A compound of Formula

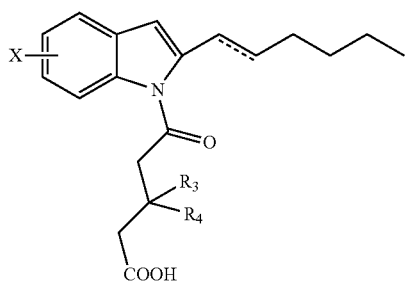

wherein X is H, halogen or alkyl; R₃ and R₄ are H and H; H and CH₃; CH₃ and CH₃ or H and ethyl; or Formula

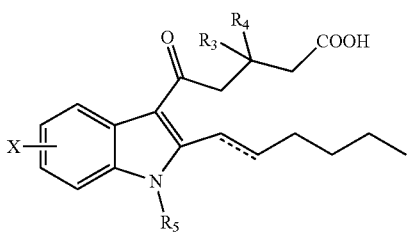

wherein X is H, halogen or alkyl; R₃ and R₄ are H and H; H and CH₃; CH₃ and CH₃ ; or H and ethyl and R₅ is H, CH₃ or CH₃CH₂;

or a pharmaceutically acceptable salt thereof.

11. A compound selected from:

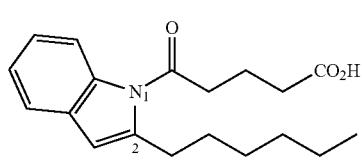

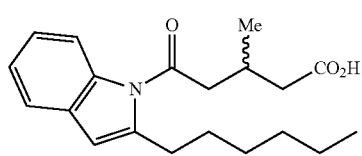

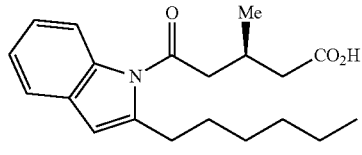

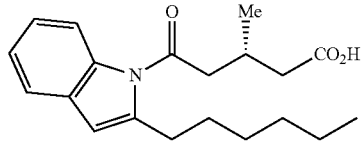

5
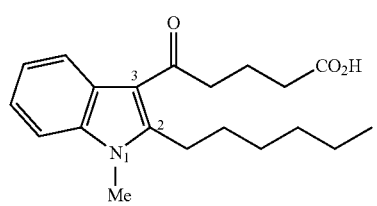
6
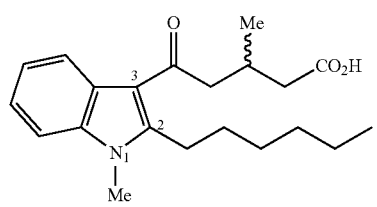
7
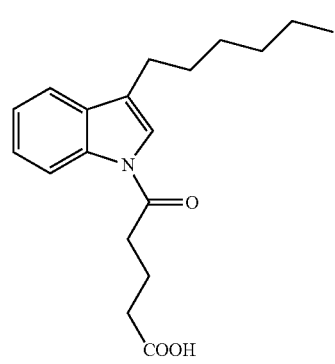
8
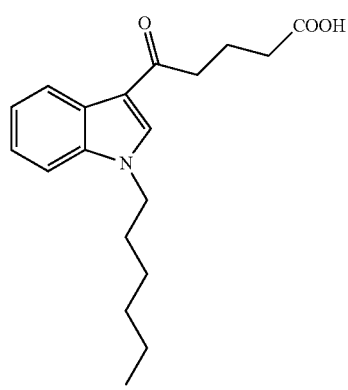
10
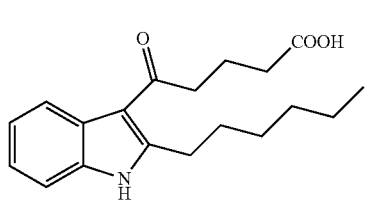
11
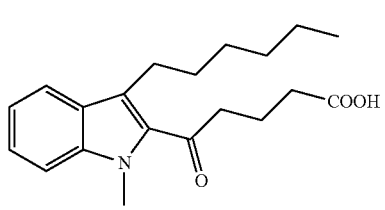
12
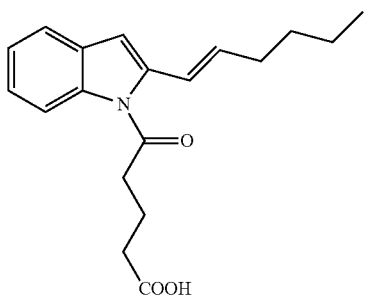
21
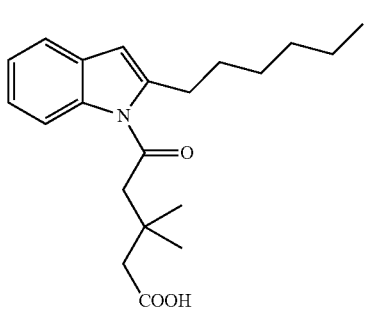
29
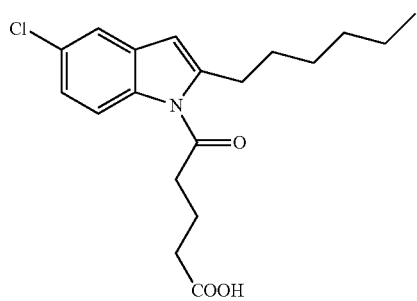
36
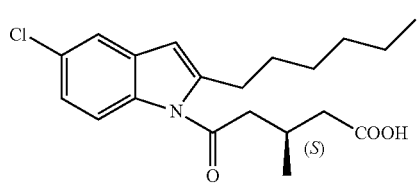
56
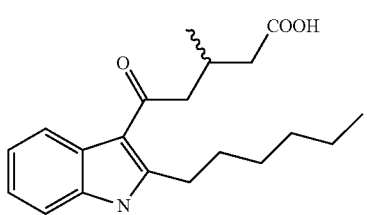
57
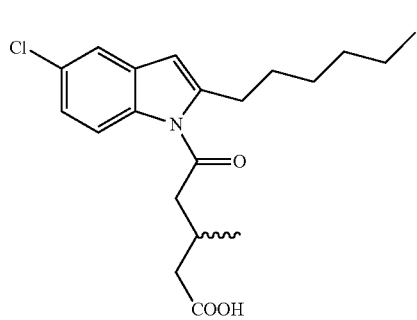

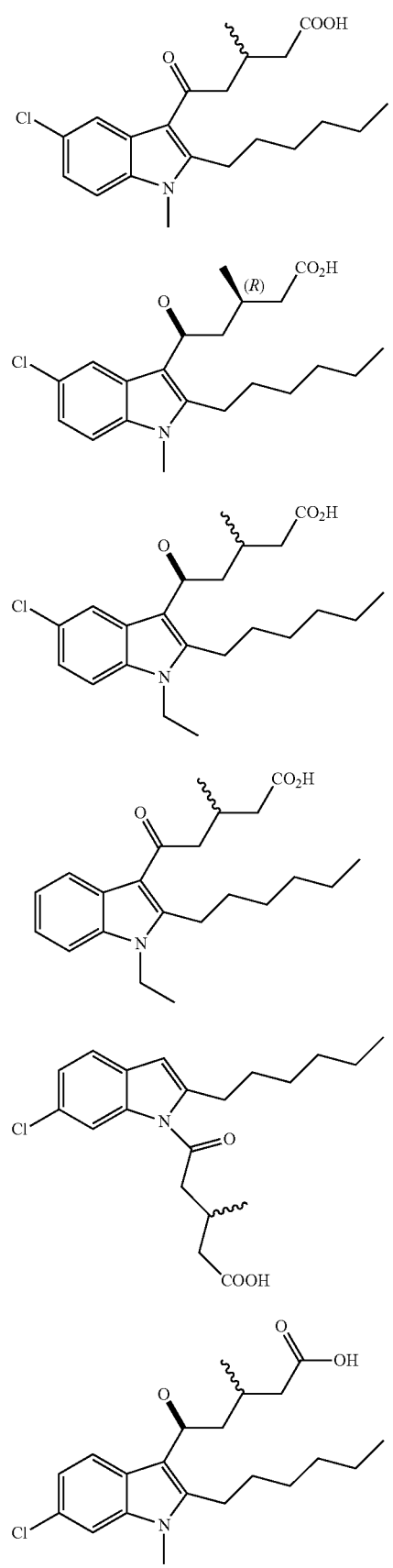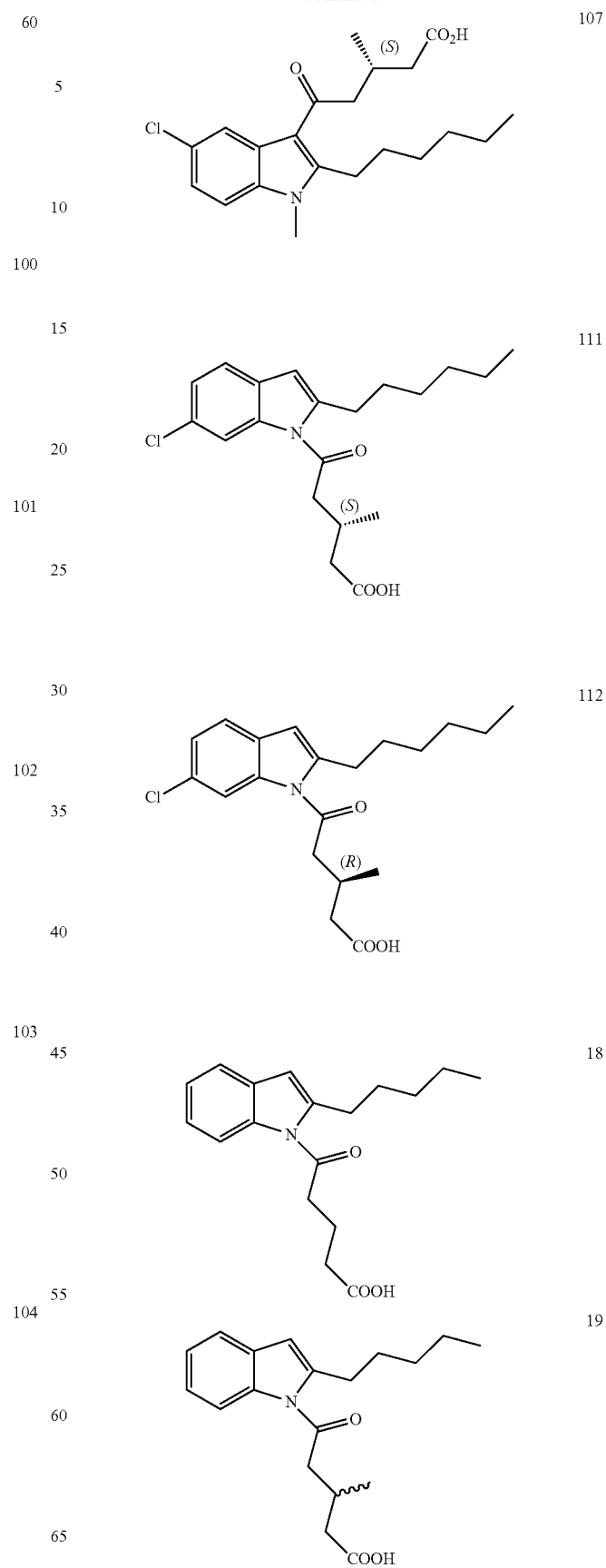

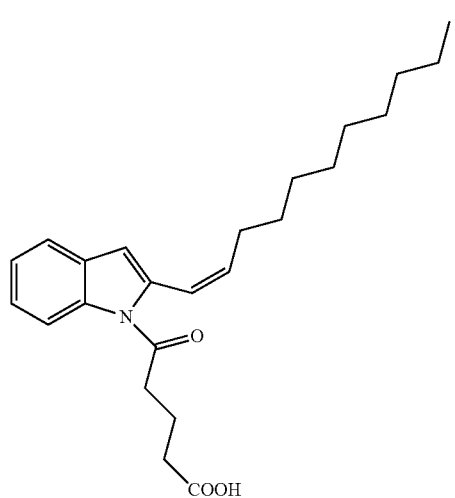
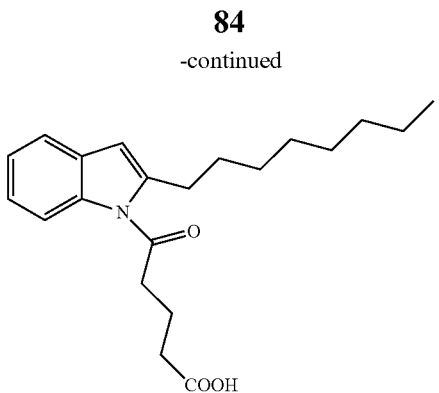
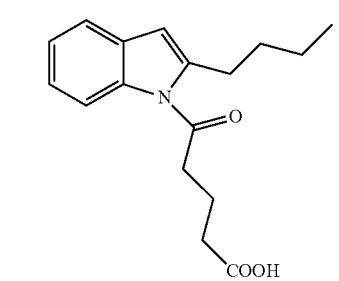
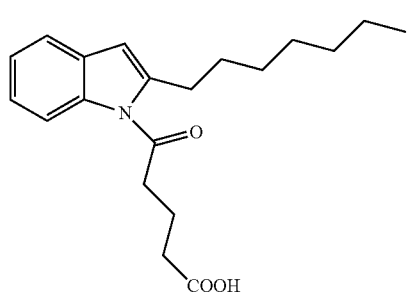
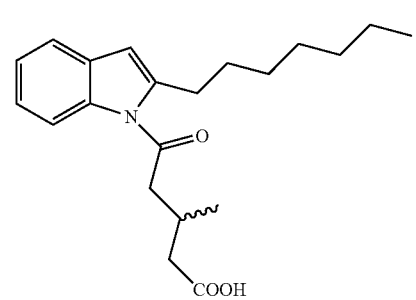
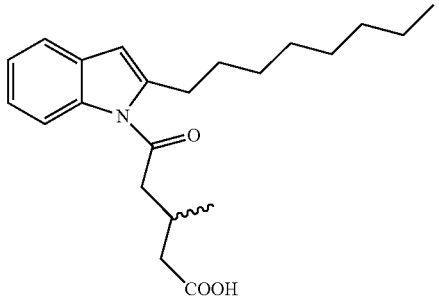

85

-continued

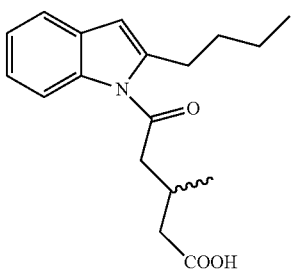

59

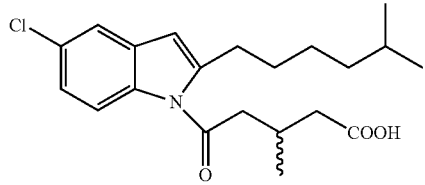

100

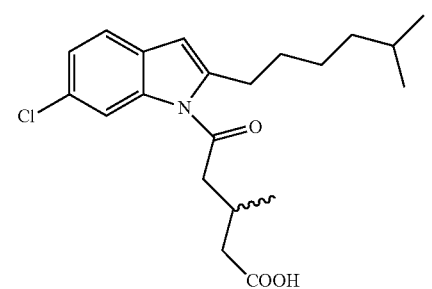

109

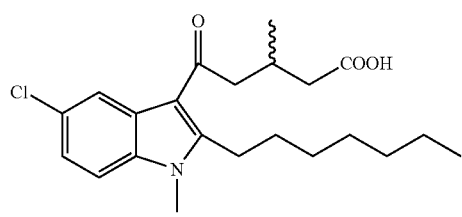

110

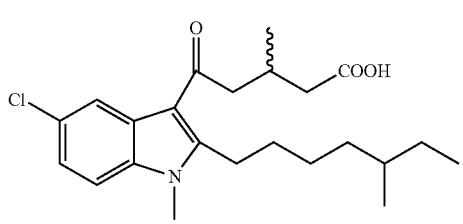

113

114 and

86

-continued

115

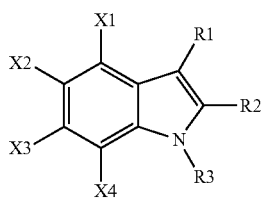

or a pharmaceutically acceptable salt thereof.

12. A compound according to claim 10, wherein the aromatic group in the compound is substituted with F, Cl, Br or I.

13. A method of treating inflammation associated with asthma, allergic rhinitis, chronic obstructive pulmonary disease or idiopathic pulmonary fibrosis in a subject comprising administering to the subject a therapeutically effective amount of a compound of Formula II:

(II)

$$\text{[indole with } X_1, X_2, X_3, X_4, R_1, R_2, R_3 \text{]}$$

wherein:

$X_1$, $X_2$, $X_3$ and $X_4$ are independently selected from the group consisting of H, halogen, alkyl group, aralkyl group and $OR_5$ wherein $R_5$ is selected from the group consisting of H, acyl, alkyl, aralkyl, alkenyl, alkoxy, aryl, haloalkyl, cycloalkyl, haloalkoxy, heterocycloalkyl, cycloalkenyl and heterocycloalkenyl, any of which may be optionally substituted; and i) $R_3$ is selected from H and an alkyl group having 4 or more carbon atoms, one of $R_1$ or $R_2$ is an alkyl group having 4 or more carbon atoms and optionally substituted with $C_{6-16}$ aryl, or $C_{3-7}$ cycloalkyl, and the other of said $R_1$ or $R_2$ is

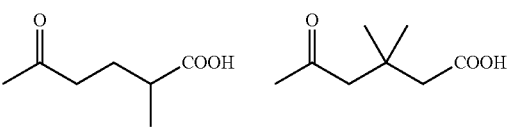

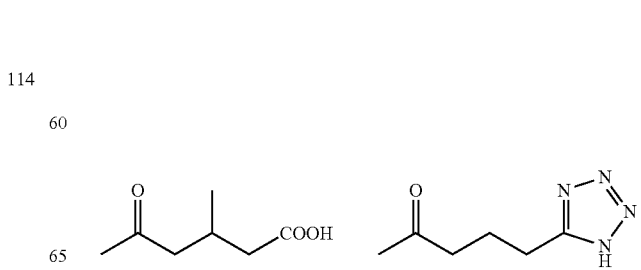

-continued

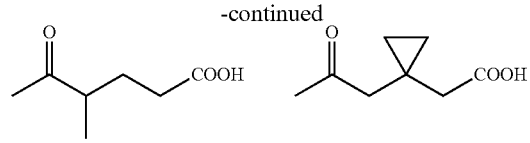

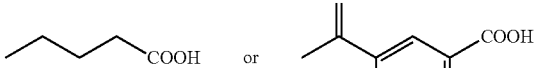

or
ii) $R_3$ is

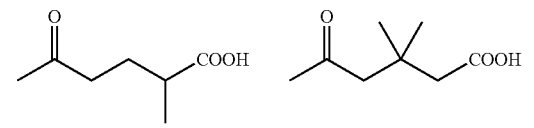

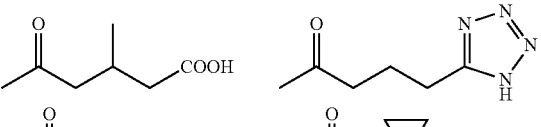

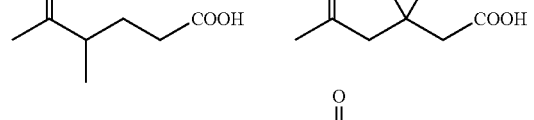

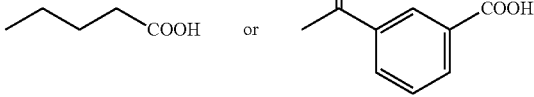

and $R_1$ is selected from H and an alkyl group having 4 or more carbon atoms, and $R_2$ is an alkyl group having 4 or more carbon atoms and optionally substituted with $C_{6-16}$ aryl, or $C_{3-7}$ cycloalkyl; or iii) $R_1$, $R_2$ and $R_3$ are each selected from H and an alkyl group having 4 or more carbon atoms, wherein at least one of $R_1$, $R_2$ and $R_3$ is an alkyl group having 4 or more carbon atoms, and at least one of $R_1$, $R_2$ and $R_3$ is

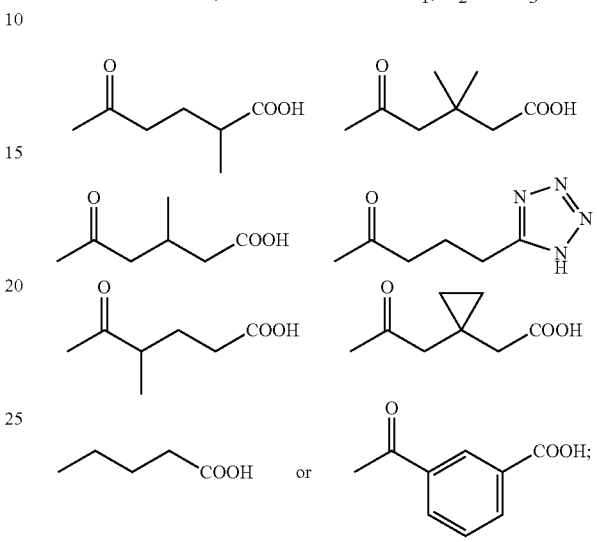

or a pharmaceutically acceptable salt thereof.

14. The method of claim 13, wherein the action of eicosanoids is inhibited.

15. The method of claim 14, wherein the eicosanoid is 5-oxo-ETE.

* * * * *